United States Patent
Saidi et al.

(10) Patent No.: US 11,826,071 B2
(45) Date of Patent: Nov. 28, 2023

(54) APPARATUS AND METHODS FOR TISSUE REDUCTION

(71) Applicant: CorIT LLC, Dunn Loring, VA (US)

(72) Inventors: Iyad Saidi, Dunn Loring, VA (US); Cameron Loper, Falls Church, VA (US); Charles M. Huck, Somerville, NJ (US); Ryan Mazurick, Alexandria, VA (US); Jonathan Whitcraft, Lancaster, PA (US)

(73) Assignee: CorIT Medical, LLC, Mclean, VA (US)

( * ) Notice: Subject to any disclaimer, the term of this patent is extended or adjusted under 35 U.S.C. 154(b) by 391 days.

(21) Appl. No.: 17/087,485

(22) Filed: Nov. 2, 2020

(65) Prior Publication Data

US 2021/0077140 A1    Mar. 18, 2021

Related U.S. Application Data

(62) Division of application No. 15/820,151, filed on Nov. 21, 2017, now Pat. No. 10,849,645.
(Continued)

(51) Int. Cl.
*A61B 17/3205* (2006.01)
*A61B 1/313* (2006.01)
(Continued)

(52) U.S. Cl.
CPC ........ *A61B 17/32053* (2013.01); *A61B 1/313* (2013.01); *A61B 17/1615* (2013.01);
(Continued)

(58) Field of Classification Search
CPC ........... A61B 2017/00353; A61B 2017/00358; A61B 2017/305; A61B 2017/2212; A61B 2017/320024; A61B 2017/320775; A61B 2017/2215; A61B 2017/2217; A61B 17/32053; A61B 17/22; A61B 17/221;
(Continued)

(56) References Cited

U.S. PATENT DOCUMENTS

| 987,173 A | 3/1911 | Sale |
|---|---|---|
| 1,891,054 A | 12/1932 | Pitman |

(Continued)

FOREIGN PATENT DOCUMENTS

| EP | 2520237 | 11/2012 |
|---|---|---|
| FR | 1378088 | 11/1964 |

(Continued)

*Primary Examiner* — Ashley L Fishback
(74) *Attorney, Agent, or Firm* — Levine Bagade Han LLP

(57) ABSTRACT

Apparatus and methods for tissue reduction are described where one embodiment of the tissue resection device may generally comprise an external clamping mechanism having at least two distally extending members shaped with an atraumatic distal end and defining a confined region between the distally extending members sized to receive a tissue region therebetween. Additionally, an elongate coring needle defining a lumen and having a proximal end attached to a handle and a distal end which defines a cutting mechanism may also be included, wherein the coring needle is translatable adjacent and/or relative to the external or internal clamping mechanism defined by the confined region.

35 Claims, 32 Drawing Sheets

Related U.S. Application Data

(60) Provisional application No. 62/435,943, filed on Dec. 19, 2016, provisional application No. 62/426,053, filed on Nov. 23, 2016.

(51) Int. Cl.

| | | |
|---|---|---|
| *A61B 17/16* | (2006.01) | |
| *A61B 17/295* | (2006.01) | |
| *A61B 17/24* | (2006.01) | |
| *A61B 90/00* | (2016.01) | |
| *A61B 17/32* | (2006.01) | |
| *A61B 17/34* | (2006.01) | |
| *A61B 17/30* | (2006.01) | |
| *A61B 17/00* | (2006.01) | |

(52) U.S. Cl.
CPC ...... *A61B 17/1637* (2013.01); *A61B 17/1688* (2013.01); *A61B 17/24* (2013.01); *A61B 17/295* (2013.01); *A61B 17/30* (2013.01); *A61B 2017/00199* (2013.01); *A61B 2017/00221* (2013.01); *A61B 2017/00734* (2013.01); *A61B 2017/246* (2013.01); *A61B 2017/320052* (2013.01); *A61B 2017/320064* (2013.01); *A61B 2017/3488* (2013.01); *A61B 2090/034* (2016.02); *A61B 2090/036* (2016.02); *A61B 2090/062* (2016.02)

(58) Field of Classification Search
CPC ...... A61B 17/320708; A61B 17/32075; A61B 17/3207; A61B 17/320758; A61B 17/32002; A61B 10/02; A61B 10/0233; A61B 10/06; A61B 2010/0208; A61B 2010/045; A61B 2017/2932; A61B 2017/2926; A61B 2017/2933; A61B 2017/294; A61B 2017/2944
See application file for complete search history.

(56) References Cited

U.S. PATENT DOCUMENTS

| | | |
|---|---|---|
| 2,137,710 A | 11/1938 | Anderson |
| 3,404,677 A | 10/1968 | Springer |
| 3,481,641 A | 12/1969 | Berger et al. |
| 3,844,291 A | 10/1974 | Moen |
| 4,258,716 A | 3/1981 | Sutherland |
| 4,427,014 A | 1/1984 | Bel et al. |
| 4,994,079 A | 2/1991 | Genese et al. |
| 5,052,402 A | 10/1991 | Bencini et al. |
| 5,318,589 A | 6/1994 | Lichtman |
| 5,370,658 A | 12/1994 | Scheller et al. |
| 5,499,997 A | 3/1996 | Sharpe et al. |
| 5,562,102 A | 10/1996 | Taylor |
| 5,573,008 A | 11/1996 | Robinson et al. |
| 5,636,639 A | 6/1997 | Turturro et al. |
| 5,638,827 A | 6/1997 | Palmer et al. |
| 5,669,927 A | 9/1997 | Boebel et al. |
| 5,782,861 A | 7/1998 | Cragg et al. |
| 5,823,971 A | 10/1998 | Robinson et al. |
| 5,951,488 A | 9/1999 | Slater et al. |
| 6,017,353 A | 1/2000 | Rankins |
| 6,142,957 A | 11/2000 | Diamond et al. |
| 6,228,023 B1 | 5/2001 | Zaslavsky et al. |
| 6,306,084 B1 | 10/2001 | Pinczower |
| 6,503,263 B2 | 1/2003 | Adams |
| 7,169,156 B2 | 1/2007 | Hart |
| 7,261,725 B2 | 8/2007 | Binmoeller |
| 7,361,168 B2 | 4/2008 | Makower et al. |
| 7,785,337 B2 | 8/2010 | Adams et al. |
| 8,500,654 B2 | 8/2013 | Goldenberg |
| 8,845,684 B2 | 9/2014 | Von Oepen |
| 8,870,893 B2 | 10/2014 | Makower et al. |
| 9,308,358 B2 | 4/2016 | Oliver et al. |
| 10,390,852 B2 | 8/2019 | Ravikumar et al. |
| 10,405,850 B2 | 9/2019 | Stewart et al. |
| 10,413,282 B2 | 9/2019 | Miller |
| 10,849,645 B2 | 12/2020 | Saidi et al. |
| 2001/0053873 A1 | 12/2001 | Schaaf et al. |
| 2003/0120305 A1 | 6/2003 | Jud et al. |
| 2003/0225344 A1 | 12/2003 | Miller |
| 2005/0250984 A1 | 11/2005 | Lam et al. |
| 2007/0213766 A1 | 9/2007 | Ravikumar |
| 2007/0282170 A1 | 12/2007 | Ravikumar |
| 2008/0039880 A1 | 2/2008 | Nohilly et al. |
| 2008/0188877 A1 | 8/2008 | Hickingbotham |
| 2008/0255597 A1 | 10/2008 | Pravong et al. |
| 2008/0319455 A1 | 12/2008 | Harris et al. |
| 2009/0287114 A1 | 11/2009 | Lee et al. |
| 2011/0178547 A1 | 7/2011 | Paul et al. |
| 2012/0150216 A1 | 6/2012 | Hickingbotham et al. |
| 2012/0209140 A1* | 8/2012 | Ryan ............... A61B 10/06 600/564 |
| 2012/0289985 A1 | 11/2012 | Motai et al. |
| 2013/0211440 A1 | 8/2013 | Schwab et al. |
| 2013/0218175 A1 | 8/2013 | Auerbach et al. |
| 2013/0325049 A1 | 12/2013 | Jang et al. |
| 2014/0277043 A1 | 9/2014 | Jenkins et al. |
| 2014/0277045 A1 | 9/2014 | Fazio et al. |
| 2015/0018837 A1 | 1/2015 | Sartor et al. |
| 2016/0000423 A1 | 1/2016 | Shields et al. |
| 2016/0058461 A1 | 3/2016 | Ravikumar et al. |
| 2018/0140319 A1 | 5/2018 | Saidi et al. |

FOREIGN PATENT DOCUMENTS

| | | |
|---|---|---|
| JP | S61-265135 | 11/1986 |
| WO | WO 2008/063156 | 5/2008 |
| WO | WO 2014/150010 | 9/2014 |
| WO | WO 2018/098187 | 5/2018 |

\* cited by examiner

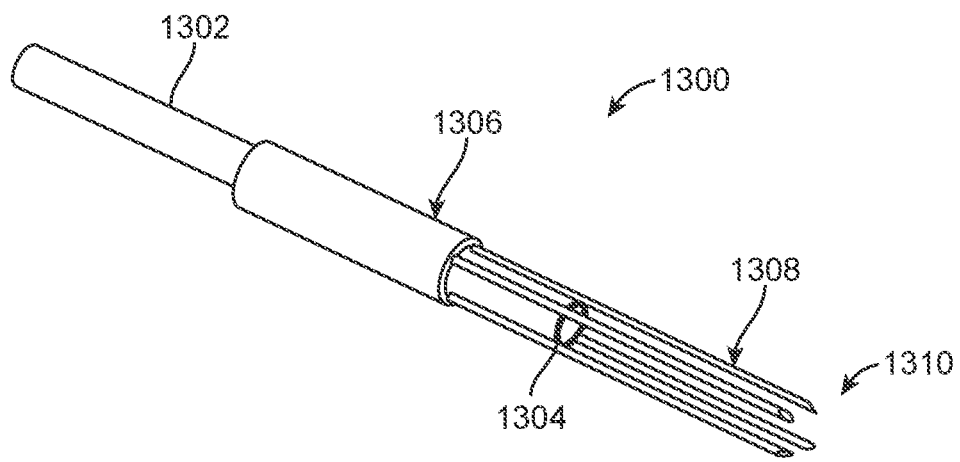
FIG. 13A
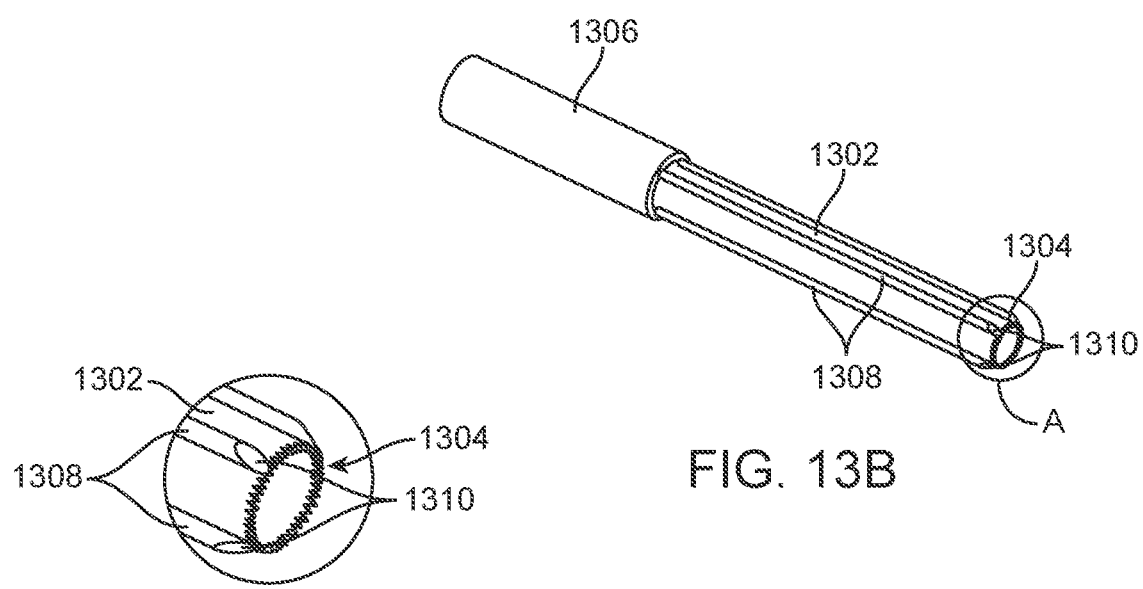
FIG. 13B
Detail A
FIG. 13C
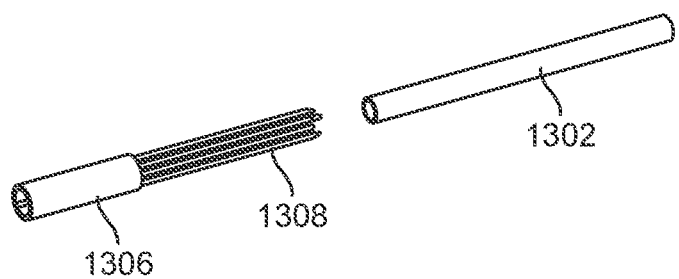
FIG. 13D

Detail A

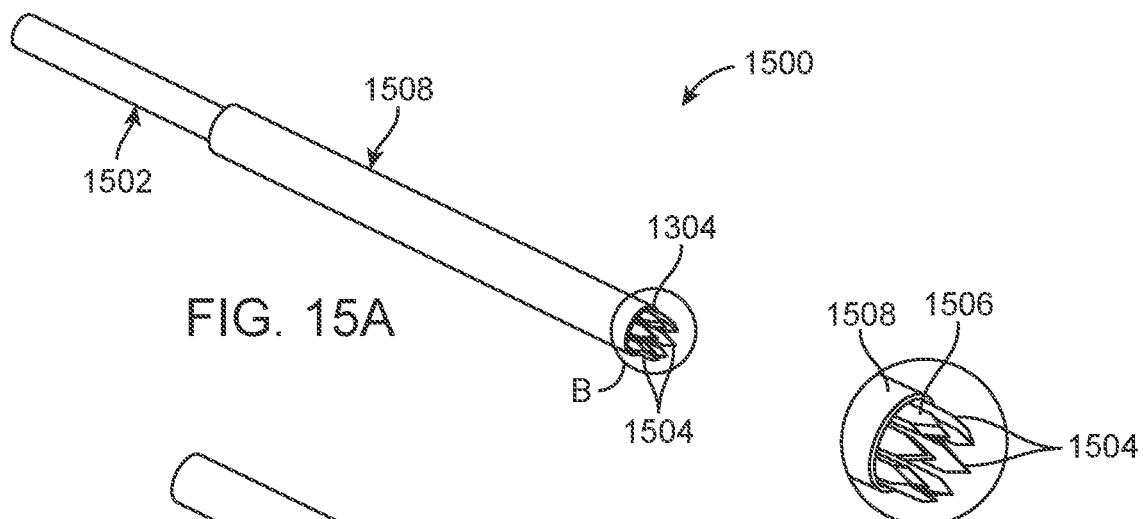
FIG. 15A
FIG. 15B
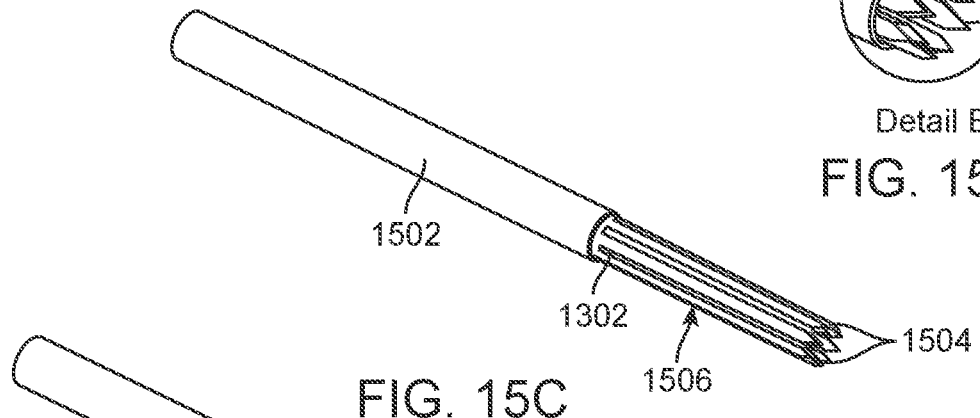
FIG. 15C
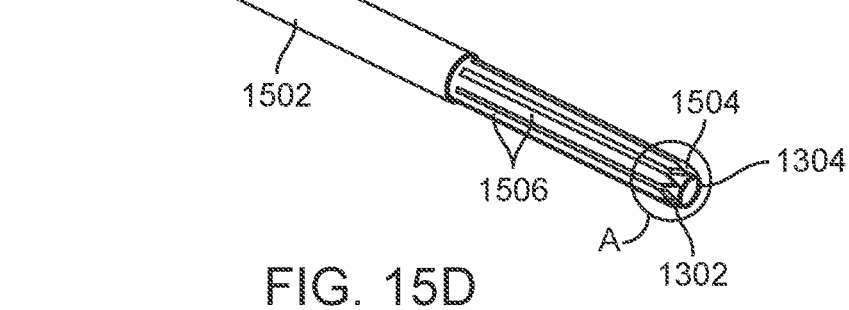
FIG. 15D
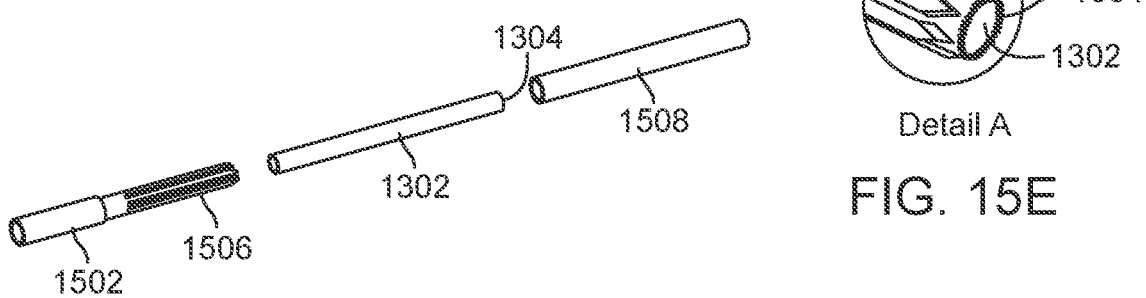
FIG. 15E
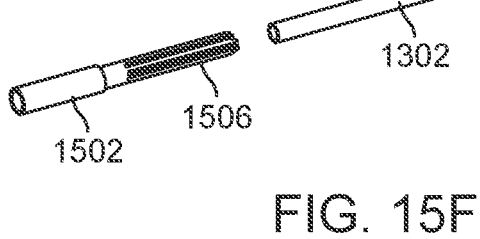
FIG. 15F

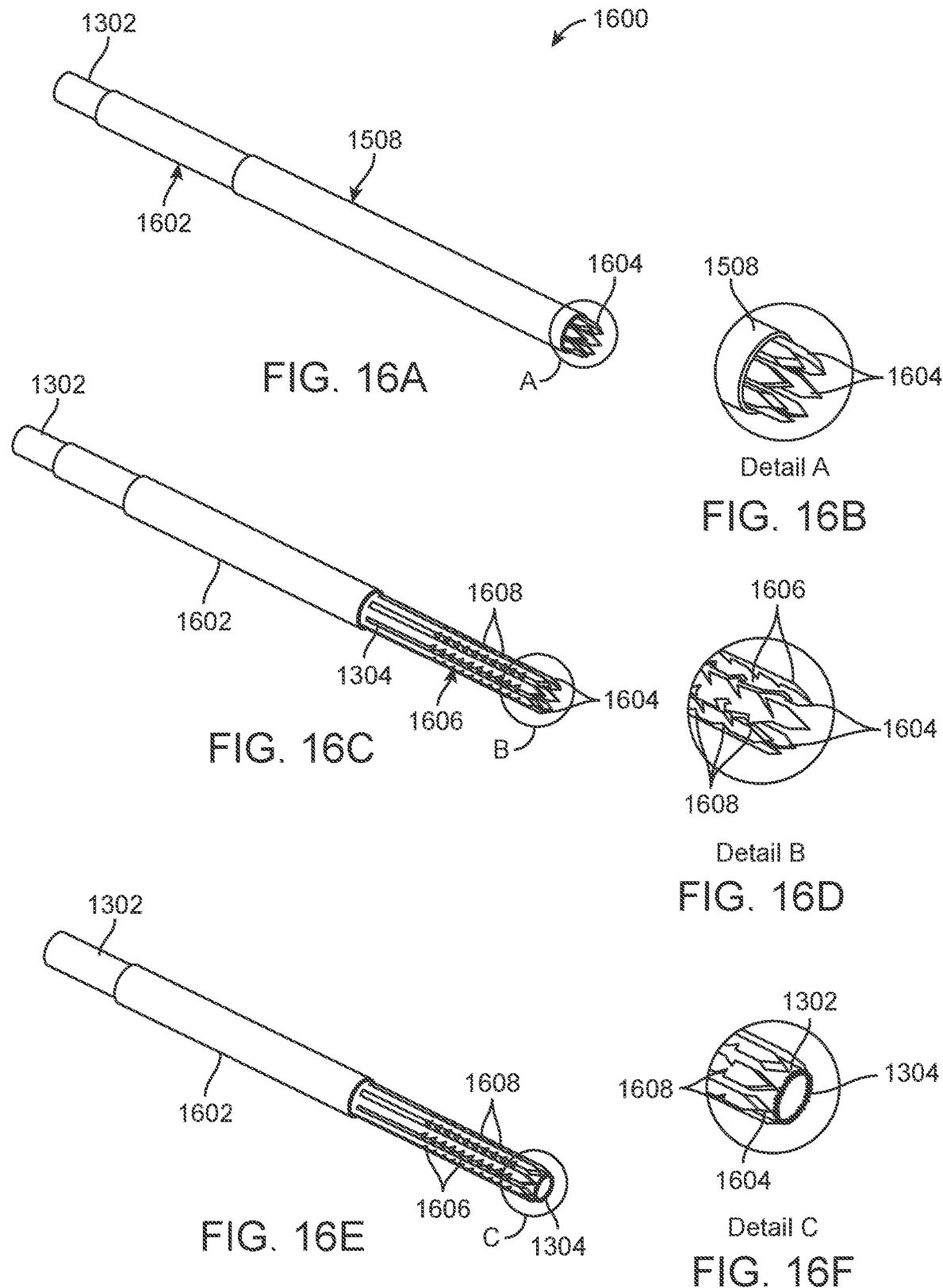

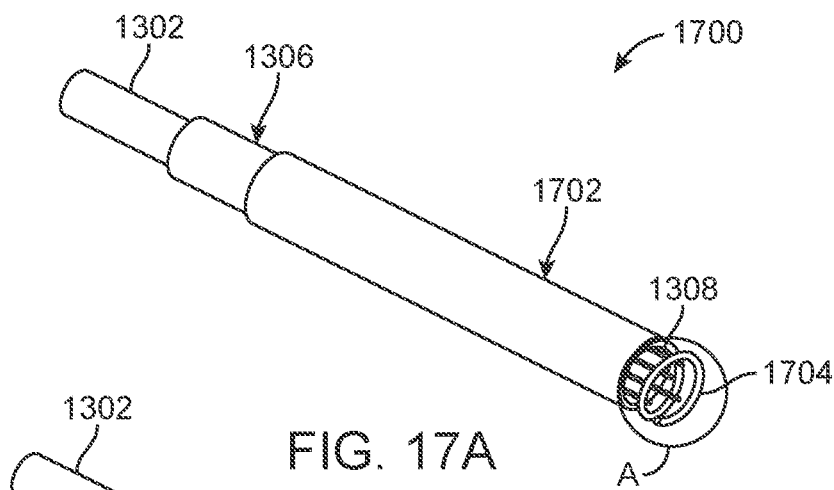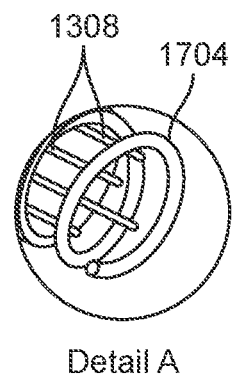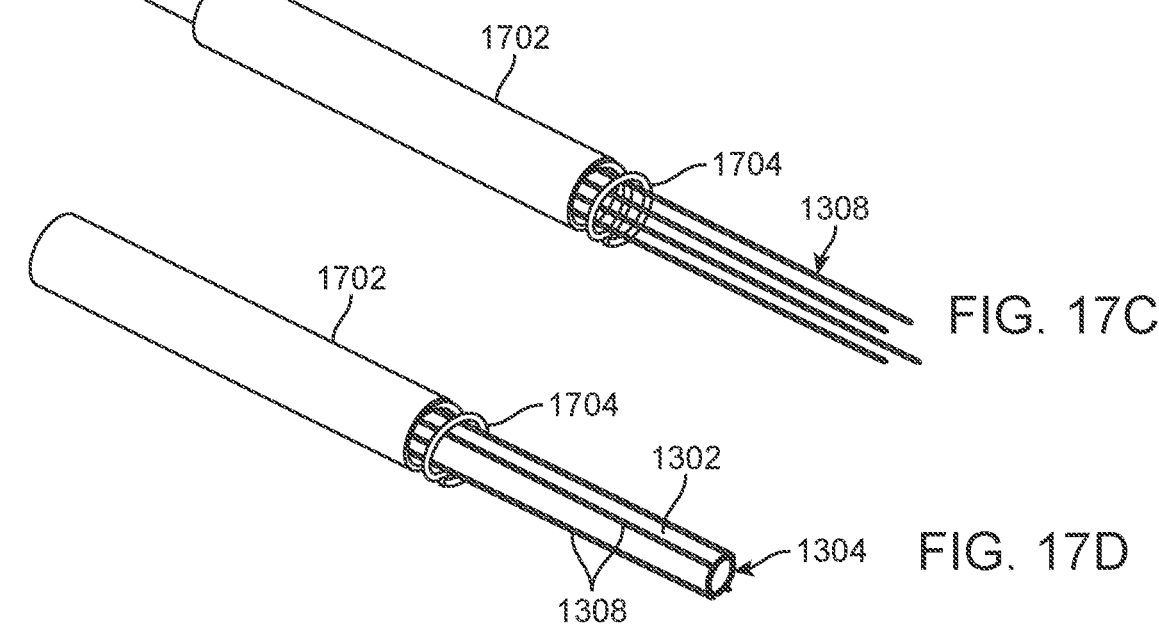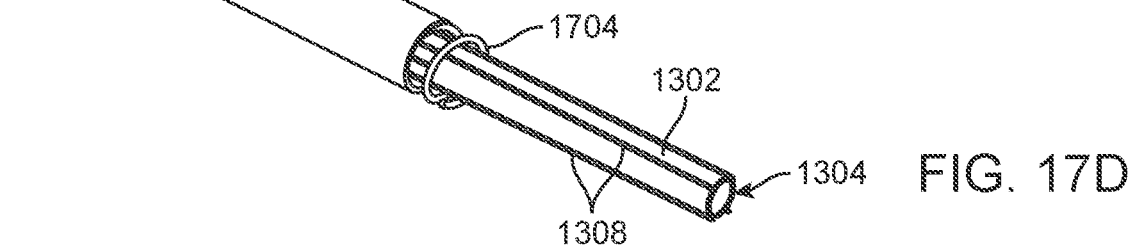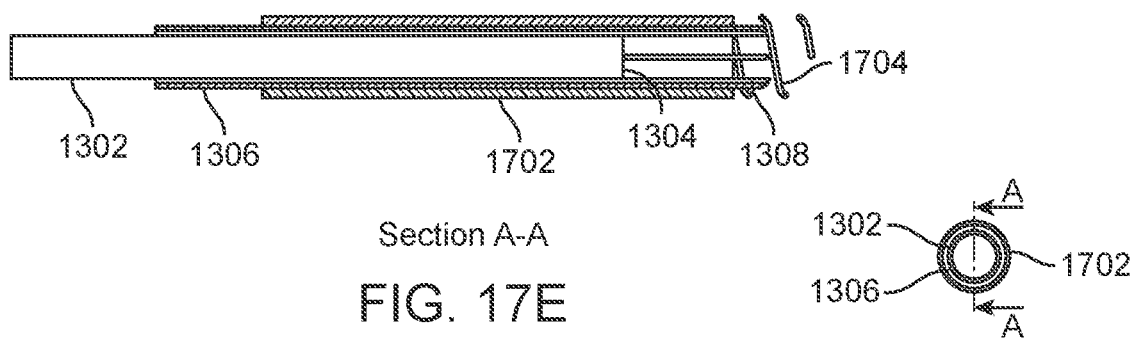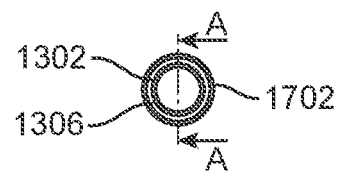

Detail A

Detail B

Section E-E

Detail A

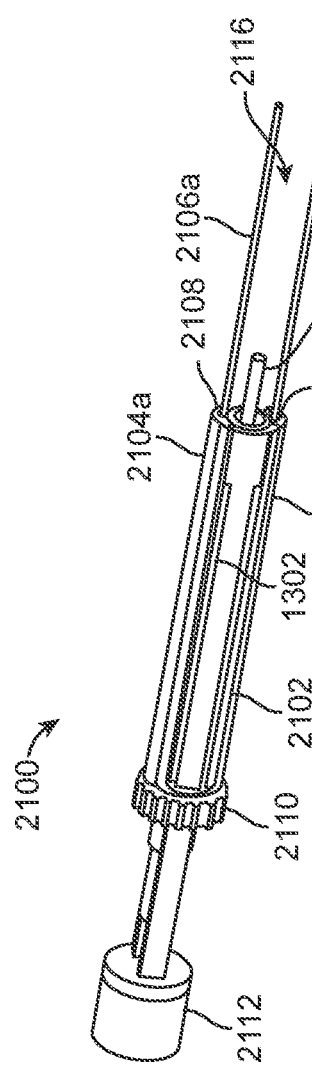
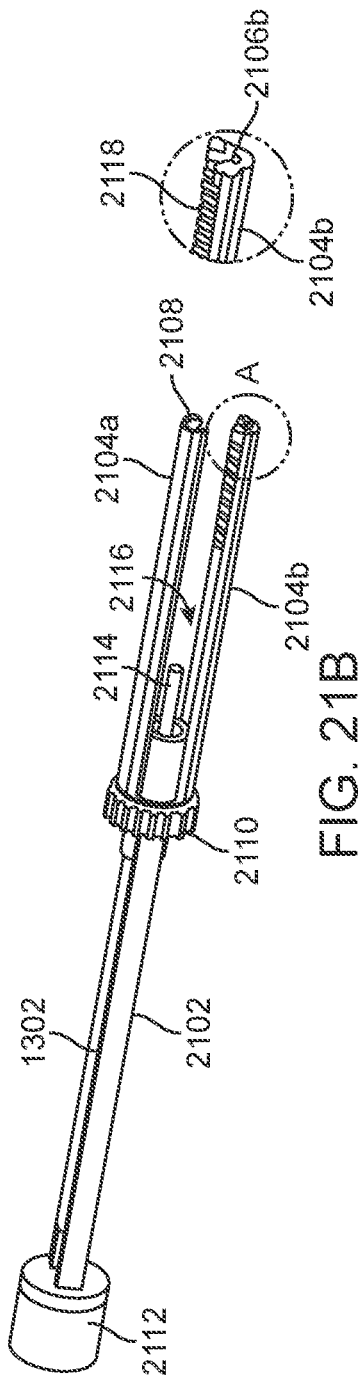
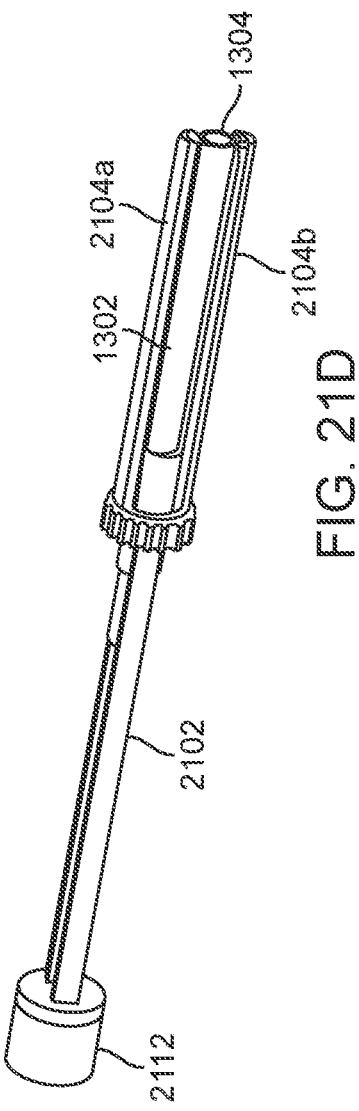

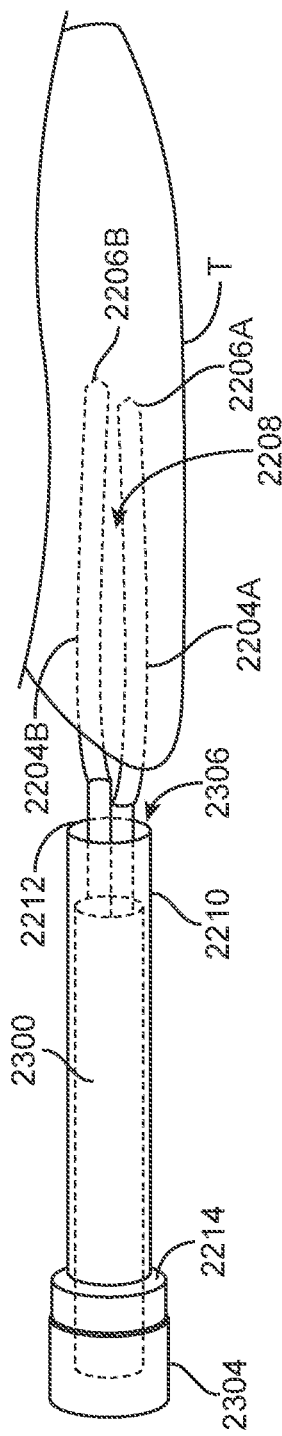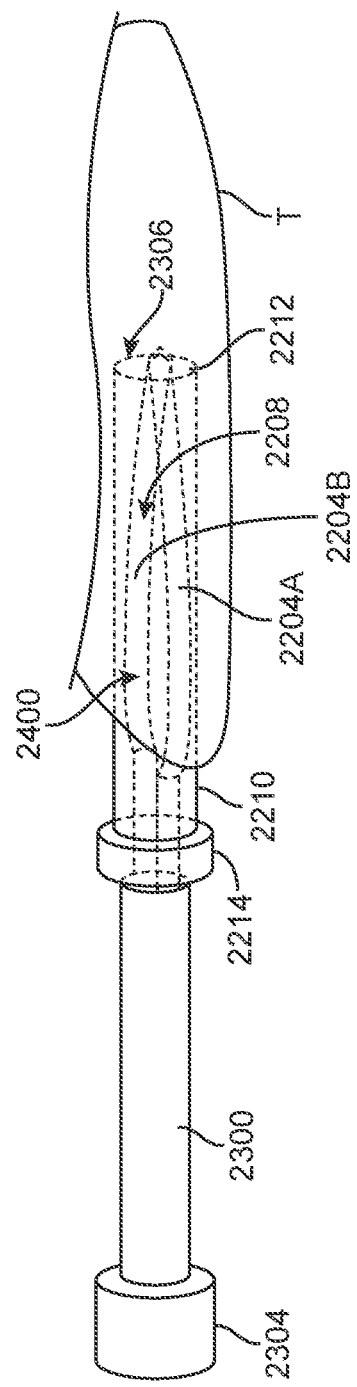
FIG. 25A
FIG. 25B

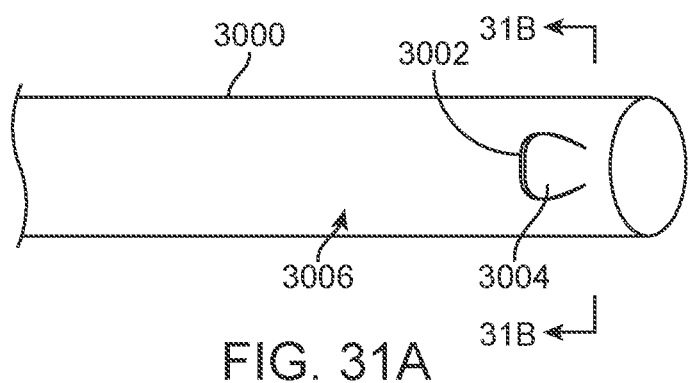 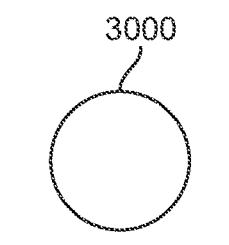
FIG. 31A    FIG. 31B
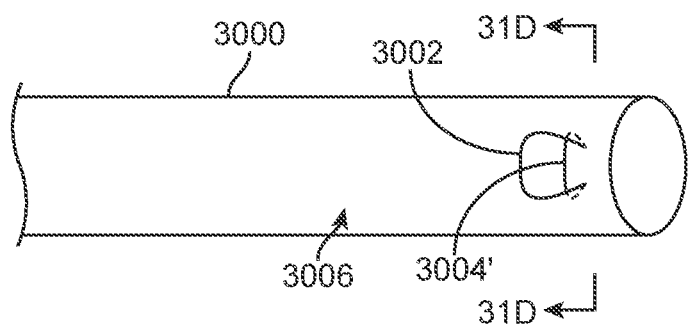 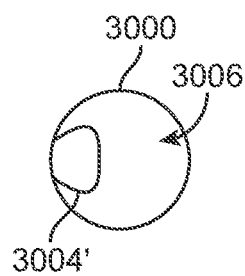
FIG. 31C    FIG. 31D

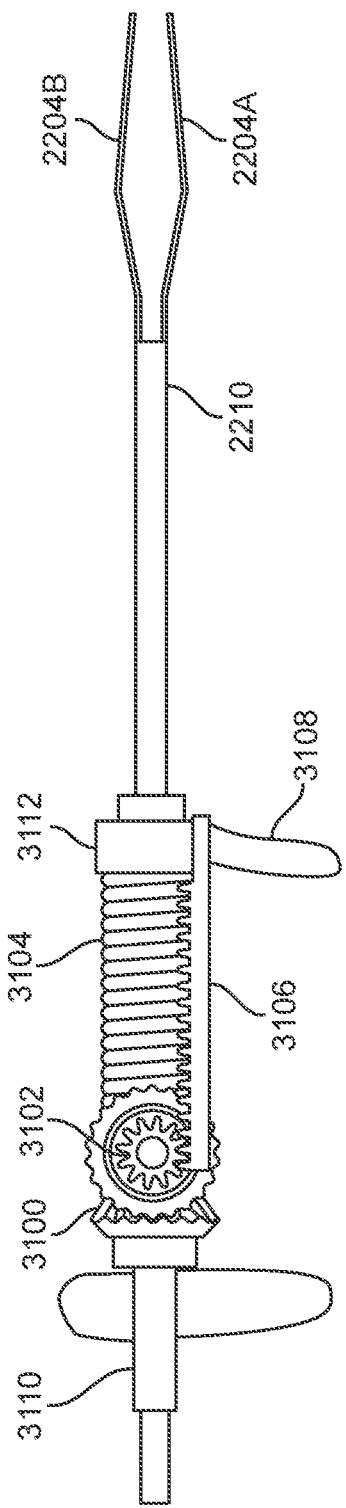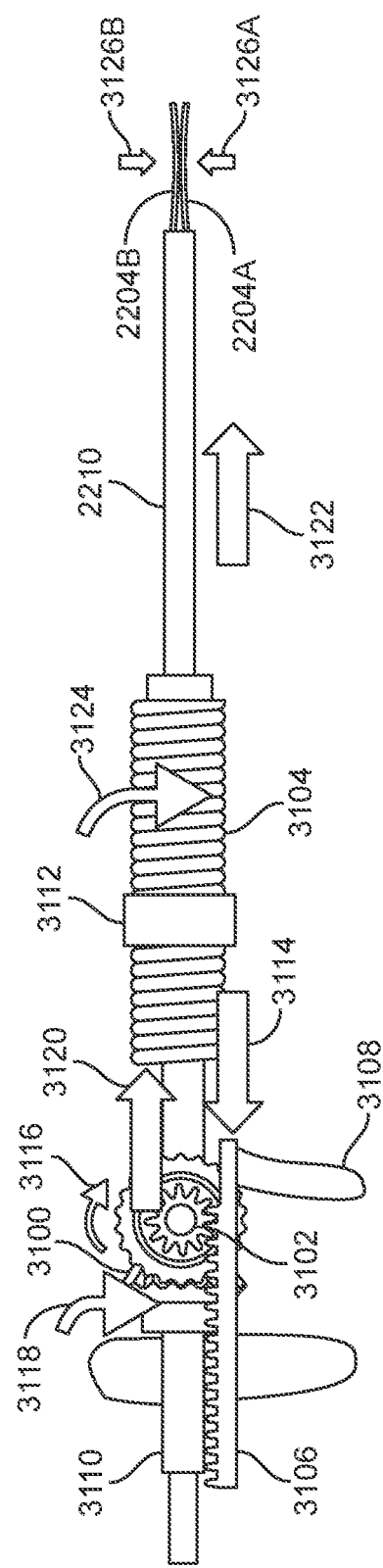
FIG. 32A
FIG. 32B

APPARATUS AND METHODS FOR TISSUE REDUCTION

CROSS-REFERENCE TO RELATED APPLICATIONS

This application is a divisional of U.S. application Ser. No. 15/820,151 filed Nov. 21, 2017, which claims the benefit of priority to U.S. Provisional Application Nos. 62/426,053 filed Nov. 23, 2016 and 62/435,943 filed Dec. 19, 2016, each of which is incorporated herein by reference in its entirety.

FIELD OF THE INVENTION

The present disclosure relates generally to an apparatus for performing coring (e.g., resection) of tissue such as the inferior turbinate tissue. Specifically, the disclosure is related to a medical apparatus and methods for coring tissues such as the turbinate tissues.

BACKGROUND OF THE INVENTION

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

The nasal mucosa plays a key role in conditioning inhaled air and in regulating the immune response. Chronic nasal obstruction is a condition frequently encountered in rhinological practice. Such a condition can interfere with social and business activities and moreover negatively affect a quality of life. The turbinate anatomy in humans includes inferior turbinate that comprise lateral tissues which direct airflow in the nose.

The turbinate tissue is primarily composed of soft tissue in which inflammation and vascular congestion leads to a condition of hypertrophy (i.e., an increase in the volume of an organ/tissue due to enlargement of its component cells). The soft tissue has a mucosal lining and may be attached to a thin bony skeleton. The soft tissue often swells and shrinks, thereby contributing to obstruction of the nasal airway. Hypertrophy of the inferior turbinate markedly affects nasal air-flow, and as such a reduction of the turbinate is necessitated in order to decrease nasal obstruction.

Submucosal inferior turbinate resection is a commonly performed medical procedure to reduce the size of the soft tissue of the turbinate. The reduction in the size of the soft tissue improves nasal airway passage. Various techniques are known to be used to reduce the size of the turbinate. One mechanism of direct resection of the turbinate tissue involves partially excising or cauterizing the tissue at the surface. However, this technique often results in deleterious physiological effects including dry nose, excessive crusting, and scarring. There is a desire to excise the submucosal tissue, while preserving the lining to the extent possible.

A further technique of resection of the submucosal tissue involves the use of powered devices such as a 'microdebrider'. The microdebrider includes suction and a rotating blade combination with which the turbinate tissue is submucosally resected. Radio-frequency electronic ablation is another technique used for resecting tissue submucosally, while attempting to preserve the surface mucosa. However, a drawback associated with the microdebrider and electronic ablation devices is that the instruments are powered, and thus require additional generation and control equipment, which increases the cost of procedure, and limits the availability of such devices only in operation theaters. From an operational standpoint, the microdebrider resects the tissues in small portions. Thus, to resect a large amount of the inferior turbinate requires a significant period of time to sequentially remove incremental small pieces of the turbinate tissue, which prolongs the procedure and causes discomfort to conscious patients and poses stringent, accurate device positioning requirements on the surgeons. Furthermore, microdebrider and electronic ablation devices have a substantial weight and incur vibrations (due to their powered nature) while in operation. Such vibrations hinder the tactile feedback provided by the devices to the surgeons.

Accordingly, there is a requirement for a turbinate tissue coring device that addresses the above described deficiencies.

BRIEF SUMMARY OF THE INVENTION

The present disclosure provides for a device to submucosally resect tissue. The device may generally include a guiding needle(s), a spiraling needle, and a coring blade that allows for precise positioning and control of the coring process, and clamping elements that secure the turbinate tissue during the coring process. Furthermore, by one embodiment of the present disclosure, the device is a non-powered instrument that provides tactile feedback from the tissue being resected, a feature that is often absent with powered medical instrumentation.

In one embodiment, the location of a desired operation (e.g., position on the inferior turbinate from where tissue is to be resected) is initially directed with the use of the guiding needle. The spiraling needle is subsequently inserted and provides a template to direct and control the coring blade, which enables resection of a chunk of the turbinate tissue in a controlled manner.

In another embodiment, the tissue resection device may generally comprise a guide body configured for insertion within a body lumen, a clamping mechanism extending from the guide body and having at least two distally extending members which define a confined region sized to receive a tissue region of interest therebetween, and/or along an elongate coring needle defining a lumen and having a distal end which defines a cutting mechanism, wherein the coring needle is translatable along the distally extending members such that the coring needle envelops the confined region.

In one method of use for resecting tissue, the method may generally comprise advancing a clamping mechanism having at least two distally extending members such that the distally extending members are clamped on opposite sides of the tissue region of interest which is maintained in a stationary position relative to the clamping mechanism, advancing an elongate coring needle having a distal end which defines a cutting mechanism between the distally extending members and into the tissue region of interest, and resecting the tissue region of interest by cutting the tissue region such that a defined volume of tissue is contained within a lumen of the coring needle.

Another embodiment of the tissue resection device may generally comprise a guide body configured to receive an imaging device, one or more anchoring members extending in apposition relative to one another from the guide body and terminating in piercing tips, the anchoring members defining a confined space within a tissue region to be resected, and an elongate coring needle defining a lumen and having a proximal end attached to the handle and a distal end which defines a cutting mechanism, wherein the coring needle is translatable between the anchoring members within the confined space.

Another embodiment of the tissue resection device may generally comprise a distal clamp mechanism formed as a shoulder or surface which extends radially from a distal end of a first tubular member, a sliding clamp mechanism formed as a second tubular member having a feature configured to engage tissue, the second tubular member being slidingly positioned around the first tubular member, and an elongate coring needle defining a lumen and having a proximal end attached to the handle and a distal end which defines a cutting mechanism, wherein the coring needle is translatable through the distal clamp mechanism.

Another embodiment of the tissue resection device may generally comprise a distal clamp having one or more projections which extend radially via corresponding longitudinal members which define slots or grooves between each of the adjacent members, and an elongate coring needle defining a lumen and having a proximal end attached to the handle and a distal end which defines a cutting mechanism, wherein the coring needle is translatable through the distal clamp mechanism.

Another embodiment of the tissue resection device may generally comprise a guide body which is translatable relative to the handle, one or more clamp guides that extend distally from the guide body, one or more clamp members which extend from a clamp lock and which are translatable over a corresponding clamp guide, and an elongate coring needle defining a lumen and having a proximal end attached to the handle and a distal end which defines a cutting mechanism, wherein the coring needle is translatable between the external clamping mechanism.

Another embodiment of the tissue resection device may generally comprise an elongate coring needle defining a lumen and having a distal end which defines a cutting mechanism, a spiraling needle having one or more blades disposed upon a distal portion of the needle, wherein the one or more blades are translatable through the lumen of the coring needle when actuated via an advancement control as the cutting mechanism is advanced distally relative to the one or more blades, and a guiding needle which is translatable through the lumen of the coring needle and the spiraling needle.

In any of the embodiments described herein, the spiraling needle may be used to cut and stabilize the tissue either prior to advancing the coring blade, or the spiraling needle may be used after insertion of the coring blade to cut the tissue prior to extraction.

In yet another variation, the clamp members may not only be clamped upon an outer surface of the tissue but they may be pierced into a portion of the turbinate tissue to be removed for clamping, holding, or maintaining the tissue from within the tissue region as well. At least two apposed clamp members may extend distally from a distal end of the elongate member and terminate in respective piercing tips while defining a clamping region between the two extending clamp members. The clamp members may also each define a curvature or angle so that the members extend distally with a slight radial curvature or angle away from and relative to one another. The curvature or angle may be embodied in any number of configurations and is not limited to any particular shape or configuration.

A coring needle having a distal cutting edge may be slidably positioned along the device and positioned proximally of the clamp members. During use, the coring needle may be positioned proximally of the clamp members as the clamp members are advanced into, e.g., the nasal cavity and directly into the turbinate tissue region of interest for treatment. The clamp members may pierce into the tissue and once suitably advanced a sufficient distance, a position of the clamp members may be maintained relative to the tissue while the coring needle may be advanced distally over the clamp members by pushing the coring needle handle. As the cutting edge is advanced distally, the coring needle (or a separate elongate element) may contact against and urge the clamp members towards one another due to their radial curvature or angle so that the tissue positioned within the clamping region between the clamp members are squeezed or secured to provide better capture or purchase of the tissue as well as providing a counter force as the cutting edge cuts the surrounding tissue. As described herein, the curvature or angle along the clamp members may be embodied in any number of different configurations and thus the curvature or angle may be located along any portion of the clamp members so long as the clamp members are urged towards one another as the coring needle (or separate elongate element) is advanced over the clamp members.

In another variation, the clamp members may include one or more features or projections defined along the clamp members which improve gripping or anchoring of the members against tissue. These features or projections may include any number of mechanisms such as teeth, barbs, mesh, etc.

During initial insertion of the clamp members into the tissue, the clamp members may remain in a relatively straightened configuration. Once the clamp members have been suitably inserted into and positioned within the tissue region, the coring needle may be advanced distally relative to the clamp members such that the members are urged towards one another against the tissue clamped between. Alternatively, the clamp members may instead be moved tangentially towards one another so that the tissue becomes pinched between the clamp members.

In another variation, each of the clamp members may have a respective leveraging member which is connected or otherwise coupled or in communication with the clamp members and extends circumferentially to define a gap opposite to the connection location. The leveraging members may form an interface surface which may be tapered along the formed gap. A plunger assembly having a handle portion and a plunger arm extending distally and terminating at distal end may be slidably positioned along the assembly in parallel with the formed gap opposite to the connecting member and clamp members.

As the plunger is moved distally, the distal end of the plunger arm may be moved into the gap defined by leveraging members. The distal end of the plunger arm may define tapered interface surfaces which are tapered in an opposite configuration relative to the interface surfaces defined by the leveraging members such that when the plunger arm is advanced, the plunger arm interface surfaces may contact the interface surfaces and force the adjacent portion of each leveraging member away from one another. As the adjacent portions of members are moved away, the leveraging members may be forced to rotate circumferentially when constrained within a lumen so that the upper portion of the leveraging members are forced to move towards one another in a tangential arc as they pivot about connecting member. In turn, the clamp members may also be forced to move towards one another tangentially so that they pinch or further clamp upon tissue positioned between.

Another variation configured to provide an additional clamping force upon tissue includes a second plunger arm which extends from the handle portion and is positioned opposite to the plunger arm. The distal end of the second plunger arm may include a tapered portion positioned at a distal end of the arm and a reduced portion positioned proximal of the tapered portion along the arm. Additionally, the upper portion of the leveraging member adjacent to where the clamp members extend may also define a tapered interface corresponding to the tapered portion of the second plunger arm.

The tapered portion of second plunger arm may be positioned distal to the interface surface of the first plunger arm such that the interface surface is either aligned with or proximal to the reduced portion of the second plunger arm. The staggering or relative positioning of these features may be adjusted so that the resulting movement of the clamp members may be sequenced accordingly depending upon the advancement of the handle portion.

In yet another variation, a concentric clamp assembly may have an outer clamp with a partially circumferential clamp portion and which is actuatable via a first handle. The outer clamp may be coaxially aligned about an inner clamp and rotated relative to the inner clamp which also has a partially circumferential clamp portion and which is actuatable via a second handle. Each of the clamp portions may define an open region within which a tissue region of interest for treatment may be positioned. The inner and/or outer handles may be rotated relative to one another such that the clamp portions are drawn or clamped upon the tissue region to maintain a position of the tissue as a separate coring needle is advanced over or within the clamp assembly. The concentric clamp assembly may be utilized with any of the coring needle variations described herein.

Another variation of a coring needle which may be advanced within or externally of any of the clamping assemblies described herein, as practicable, may include a coring needle having an integrated blade. The coring needle body may define a lumen within and may also have a reconfigurable blade along a side portion of the needle body. The blade may be defined by a slit or groove which extends at with a curvature or at an angle relative to the needle body. The needle body may be advanced within the tissue either within a lumen of a clamping assembly or externally of a clamping assembly and as the needle body is advanced distally, the blade may maintain its closed configuration to present a relatively smooth surface to the tissue. However, when the needle body is retracted proximally within the tissue, the tip of the blade may gain purchase into the tissue and retract further within the lumen and into its extended configuration into the tissue as the needle body is further pulled proximally. Yet another variation of a coring needle may also include a coring needle having an integrated blade shaped in a leaf-like configuration.

Furthermore, although the devices and methods described herein may be disclosed in the context of turbinate tissue, the devices are not limited to use with turbinate tissues within the nasal cavities. Rather, the devices described may be used in any number of other tissue types or other regions of the body, e.g., liver, bone marrow, lungs, various muscle tissues, etc.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

Various embodiments of this disclosure that are proposed as examples will be described in detail with reference to the following figures, wherein like numerals reference like elements, and wherein:

FIGS. 13A to 13D illustrate various perspective views of yet another embodiment of the coring device having multiple anchoring needles;

FIGS. 15A to 15F illustrate various perspective views of yet another embodiment of the coring device having multiple blades;

FIGS. 16A to 16F illustrate various perspective views of yet another embodiment of the coring device having multiple blades with cutting and anchoring features;

FIGS. 17A to 17F illustrate various perspective views of yet another embodiment of the coring device having multiple anchoring needles and an additional tissue anchor;

FIGS. 21A to 21D illustrate various perspective views of yet another embodiment of the coring device having a clamping guide mechanism.

FIGS. 25A and 25B illustrate exemplary perspective views of one variation of the device in use.

FIGS. 31A to 31D illustrate yet another variation of a coring needle which may also be used with any of the clamping assemblies described herein.

FIGS. 32A and 32B illustrate exemplary views of another device variation which incorporates a mechanism which in turns rotates and advances the coring needle over the clamps.

DETAILED DESCRIPTION OF THE INVENTION

Figure 1:
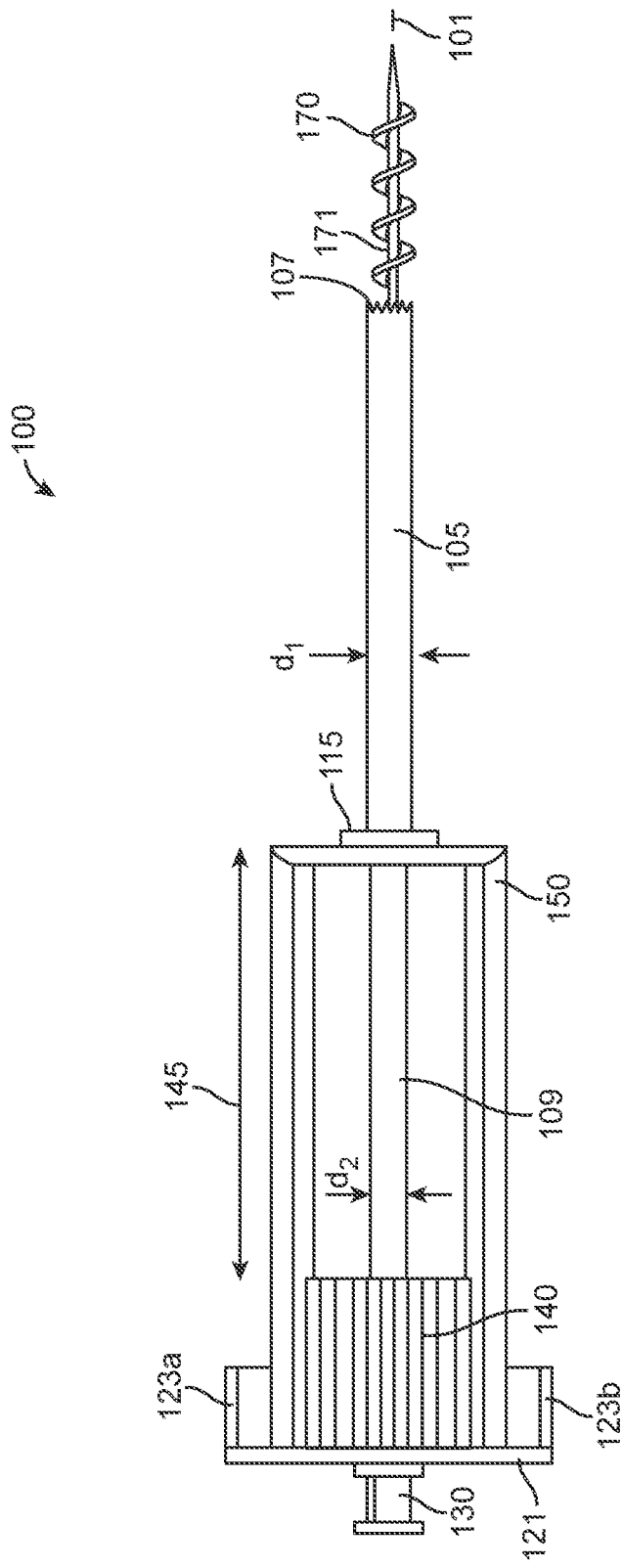
FIG. 1 depicts an exemplary turbinate coring device, according to one embodiment.

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

While aspects of the present disclosure have been described in conjunction with the specific embodiments thereof that are proposed as examples, alternatives, modifications, and variations to the examples may be made. It should be noted that, as used in the specification and the appended claims, the singular forms "a," "an," and "the" include plural referents unless the context clearly dictates otherwise.

The embodiments are mainly described in terms of particular processes and systems provided in particular implementations. However, the processes and systems will operate effectively in other implementations. Phrases such as "an embodiment", "one embodiment" and "another embodiment" may refer to the same or different embodiments. The embodiments will be described with respect to methods and compositions having certain components. However, the methods and compositions may include more or less components than those shown, and variations in the arrangement and type of the components may be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by the appended claims.

Furthermore, where a range of values is provided, it is to be understood that each intervening value between an upper and lower limit of the range- and any other stated or intervening value in that stated range is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. The following definitions are intended to aid the reader in understanding the present disclosure, but are not intended to vary or otherwise limit the meaning of such terms unless specifically indicated.

Furthermore, although the devices and methods described herein may be disclosed in the context of turbinate tissue, the devices are not limited to use with turbinate tissues within the nasal cavities. Rather, the devices described may be used in any number of other tissue types or other regions of the body, e.g., liver, breast, bone marrow, lungs, various muscle tissues, etc. for any number of procedures such as tissue biopsy, tissue reduction, etc.

Turning to FIG. 1, there is depicted an exemplary turbinate coring device 100 according to one embodiment of the present disclosure. The turbinate coring device 100 includes a handle or body portion 150 (also referred to herein as a frame) that provisions for a user of the device 100, a means or housing to hold the device 100. As shown in FIG. 1, the turbinate coring device 100 may include a back-cap 121 that is removably affixed to the frame 150. Specifically, by one embodiment, the frame 150 may include a first support member 123a, and a second support member 123b, which are affixed at opposite sides of the frame 150, respectively, as shown in FIG. 1. The support members 123a, 123b may be affixed at other locations relative to one another in other embodiments. Moreover, the back-cap 121 may be affixed (e.g., in a removable manner) to the support members 123a and 123b by a securement mechanism such as a snap-lock mechanism.

Further, the turbinate coring device 100 includes a coring needle 105 attached to a lower end of the frame 150. By one embodiment, the coring needle 105 may be affixed to the frame 150 via an attachment mechanism 115 such as a screw mechanism. It is appreciated that the attachment mechanism 115 provisions for the detachment and replacement (discussed later) of the coring tube 105. Alternatively, by one embodiment, the coring needle 105 may be permanently attached to the frame 150. The coring needle 105 is affixed to the frame 150 at a proximal end (e.g., via the attachment mechanism 115), and includes a cutting mechanism 107 such as a blade configuration at a distal end. As shown in FIG. 1, the cutting mechanism 107 of the coring needle may be a saw-tooth like arrangement. However, as described later herein, it must be appreciated that the blade configuration may include other types of configurations as well.

The coring needle 105, in this and any of the embodiments described herein, may have features to independently rotate and advance as manipulated by the operator. It may have features to incrementally advance and/or rotate in a stepwise fashion as controlled by the operator. The coring element may have gears/wheels which provide a mechanical advantage to the operator while performing the coring process. An electromechanical element may be attached to the coring element. This may be used to provide vibratory movement of the coring element, such as ultrasonic vibration, which can assist with the coring process, particularly when used with a controller, as described in further detail herein. The electromechanical element may be used to provide a rotatory or oscillatory motion of the coring element.

Figure 2:
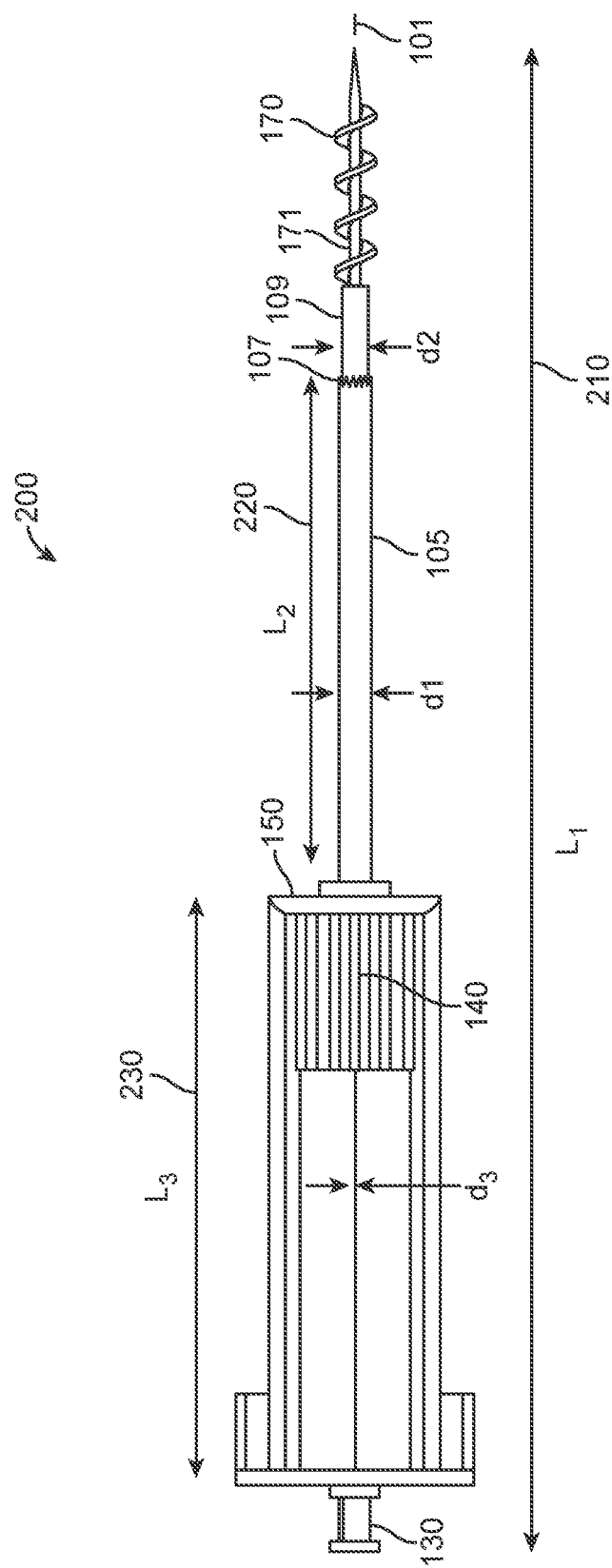
FIG. 2 depicts the turbinate coring device of FIG. 1, with a spiraling needle being disposed by rotation of a knob.

The frame 150 of the turbinate coring device 100, houses an advancement control 140 such as a knob that is designed to be movable (e.g., via a twist and turn operation) within the frame 150. The advancement control 140 includes a spiraling tube 109 affixed to its lower end. The spiraling tube 109 houses a spiraling needle 171 (shown in FIG. 2), which has at least one blade or a plurality of blades disposed thereon. Specifically, as shown in FIG. 2, the spiraling needle 171 includes blades 170 that may be disposed in a helical fashion in one embodiment. As described later herein, the spiraling needle 171 may include blades that are disposed in different configurations.

As shown in FIG. 1, the advancement control 140 is depicted at a proximal end of the frame 150. Upon advancing the control 140 such as by performing a rotation (e.g., a twist and turn operation), the control 140 is displaced along a length 145 of the frame 150. In doing so, the spiraling tube 109 that is affixed to the knob 140 is also displaced, thereby projecting the spiraling needle (shown in FIG. 2) distally beyond the cutting mechanism 107. By one embodiment of the present disclosure, the coring needle 105 has a first diameter represented as 'd1', the spiraling tube 109 has a second diameter represented as 'd2', wherein d2 is less than d1 (i.e., d2<d1) to allow for the relative movement of the spiraling tube 109 through the coring needle 105. As shown in FIG. 1, the spiraling tube 109 may be coaxially disposed with respect to the coring needle 105. Thus, upon performing the rotation of the control 140, the spiraling tube 109 moves laterally within the coring needle 105, to project the spiraling needle 171 (as shown in FIG. 2). Furthermore, as described later, it is appreciated that the spiraling tube 109 and the spiraling needle 171 (along with the spiraling blades 170) are not restricted in being two separate entities. Rather, the turbinate coring device 100 may include a single spiraling needle as shown in FIGS. 4A to 6B.

Further, the turbinate coring device 100 may include a guiding needle 101 that is affixed at a proximal end to a guiding needle knob 130. The guiding-needle-knob 130 may be affixed to the back-cap 121 via a lure lock mechanism. As such, the guiding needle 101 may be detached from the turbinate coring device 100 for replacement purposes. As shown in FIG. 1, the guiding needle 101 has a diameter represented as 'd3', wherein with respect to the diameters of the coring needle 105 (i.e., d1), and the spiraling needle tube (i.e., d2), the following condition is valid: d1>d2>d3.

By one embodiment, a location of desired operation is initially directed with the help of the guiding needle 101. Further, the spiraling needle 171 is subsequently positioned (via rotation of the control 140) to advance into the tissue. The spiraling needle 171 (of FIG. 2) can be screwed into the tissue as directed by the geometry of the spiraling blades 170. As described later, the spiraling blades can have different shapes. However, regardless of the shape of the spiraling blades, the function of the spiraling needle is to affix the needle into the turbinate tissue, and thereby provide a template to direct and control for the coring needle 105.

Upon the spiraling needle 171 being affixed into the turbinate tissue, the coring needle 105 can be introduced, to core the turbinate tissue in a controlled manner. The coring needle 105 includes blade configuration 107 that cuts the tissue as the coring needle 105 is advanced into the turbinate tissue. The coring needle 105 may be advanced in a spiraling manner (e.g., by rotating the turbinate coring device 100) and/or by detaching the coring needle 105 from the attachment mechanism 115, and further directly advancing the coring needle 105 into the turbinate tissue while the spiraling needle 171 engaged to the tissue provides an anchoring or counter-force to enable the controlled advancement of the coring needle 105 into the tissue. Note that as the coring needle 105 may be inserted into the turbinate tissue (e.g., in the spiraling fashion), the coring needle 105 stores the extracted tissue in the tubular portion of the coring needle 105. Upon the coring needle 105 being completely inserted into the inferior turbinate, an entire continuous volume or chunk (as opposed to small pieces of the turbinate tissue) of the turbinate tissue can be extracted in a single insertion.

FIG. 2 depicts the turbinate coring device of FIG. 1, with a spiraling needle advanced by rotation of a control 140. The control 140 is depicted in FIG. 2 to be disposed at an extreme distal end along the length of the frame 150. The turbinate coring device 200 as depicted in FIG. 2 has a total length 210 depicted as L1. The length 220 of the coring needle 105 is depicted as L2, and the length 230 of the frame 150 is depicted as L3. By one embodiment, the length L1 can be in the range 15-20 cms, the length L2 can be in range 5-8 cms, and the length L3 can be in the range 4-7 cms. According to one embodiment, the frame may be made of a rigid metal such as titanium, a rigid material such as ceramic, a synthetic material such as thermoplastic and the like. Any number of other suitable materials may be used to fabricate the components in other embodiments.

Figure 3:
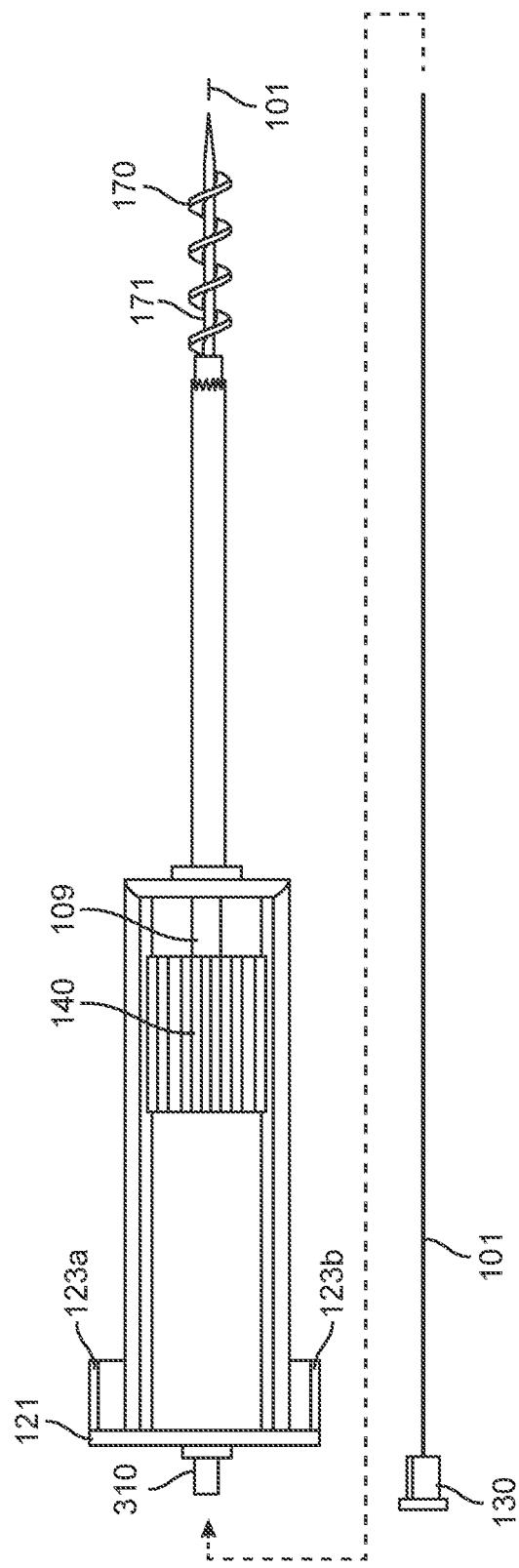
FIG. 3 depicts an exploded side view of the turbinate coring device.

Turning to FIG. 3, there is provided an exploded view of the turbinate coring device 100. As shown in the exploded view, the guiding needle 101 is affixed to the guiding needle knob 130. By one embodiment, the guiding needle knob 130 may be detached from the screw 310 in order to replace the guiding needle 101. In a similar manner, the back-cap 121 may be detached from the support members 123a and 123b, in order to replace the spiraling tube 109 which houses the spiraling needle 170. Note that although the spiraling needle 170 is shown in FIG. 3 to be housed in a spiraling tube 109, by one embodiment, the turbinate coring device may include a single tapered piece of single spiraling needle as shown below. Moreover, as shown below, the spiraling blades 171 of the spiraling needle may assume different shapes.

Figure 4A:
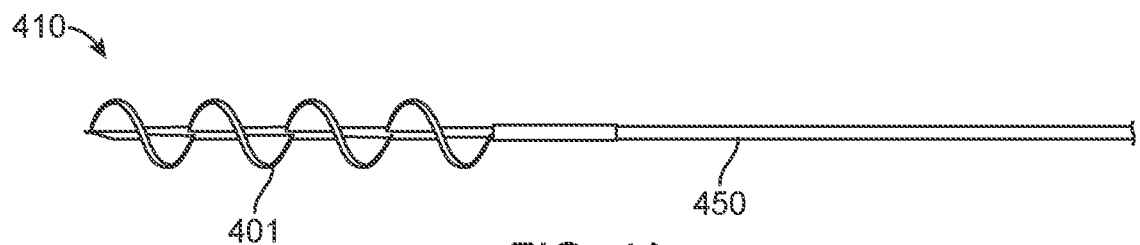
FIGS. 4A to 4C illustrate various shapes of spiraling needles.

FIG. 4A depicts according to an embodiment, a spiraling needle included in the turbinate coring device of the present disclosure. The spiraling needle configuration 410 may include a single needle having a body 450 which may be tapered, and a plurality of blades 401 disposed on the body of the spiraling needle 450. The configuration of needles 401 is a helical configuration where the blades form a continuous helical shape.

Figure 4B:
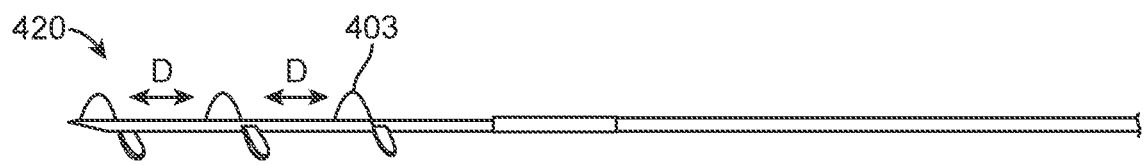
Figure 4C:
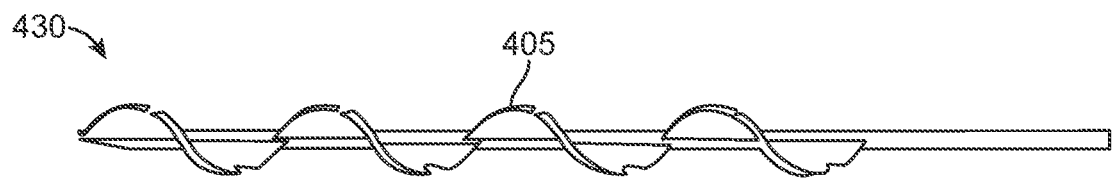

The configuration 420 depicted in FIG. 4B illustrates a spiraling needle including blades 403 that are separate and distinct from one another such that the individual blades 403 are separated by a predetermined distance 'D'. The configuration 420 incurs the advantageous ability of using less blade material, and also provides less resistance to the spiraling needle as it is inserted into the turbinate tissue. The body 450 may alternatively include just a single blade or two blades. Further, the configuration 430 depicted in FIG. 4C includes the spiraling blades being disposed in a barbed-wire like configuration 405. Such a blade configuration provides a better capture of the turbinate tissue and furthermore provides an efficient template to direct and control the coring blade.

Figure 5A:
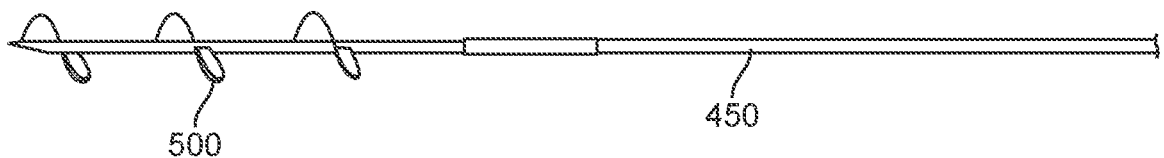
FIGS. 5A and 5B illustrate additional embodiments of spiraling needles.
Figure 5B:
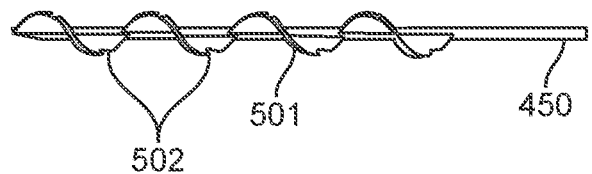

In yet another embodiment shown in FIG. 5A, the needle body 450 may include blades which are composed of three helical screw elements 500 to comprise the helical screw. The helical screw may include only one, or up to multiple screw elements (three shown here) which are separated from one another for reducing frictional resistance when advanced through the tissue as well as provided less material in fabricating the blades. In the alternative embodiment shown in FIG. 5B, one or more of the blades or the helical screw 501 may have features 502 on it, such as the barbs shown here, which are made to capture and hold the tissue during the coring process to prevent the blades from backing out from the engaged tissue, particularly when the coring needle is advanced for coring the tissue.

Figure 6A:
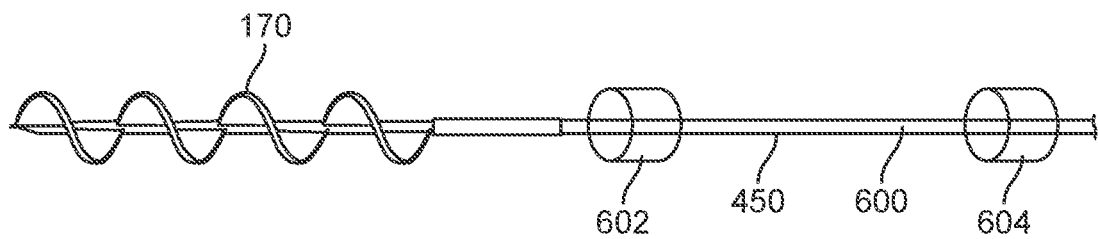
FIGS. 6A and 6B illustrate further embodiments of spiraling needles.

FIG. 6A shows yet another embodiment of a spiraling needle having one or more blades 170. The needle body 450 may define an insertion lumen 600 through which an introducing needle may be advanced. The needle body 450 may further incorporate one or more stop elements or markers 602, 604 to indicate an appropriate depth of insertion relative to the tissue. The one or more stop elements 602, 604 may be used to provide a stopping mechanism against, e.g., frame 150, such that the blades 170 and spiraling needle 171 can be extended at a predetermined distance into the tissue. Alternatively and/or additionally, the needle body 450 may define or incorporate one or more markings or gradations along the length of the needle body 450 to provide to the practitioner an indication of insertion depth of the spiraling needle 171 into the tissue. The markers 602, 604 may alternatively and/or additionally be used to guide the trajectory of the needle body within the coring blade, or similar tubular structure.

Figure 6B:
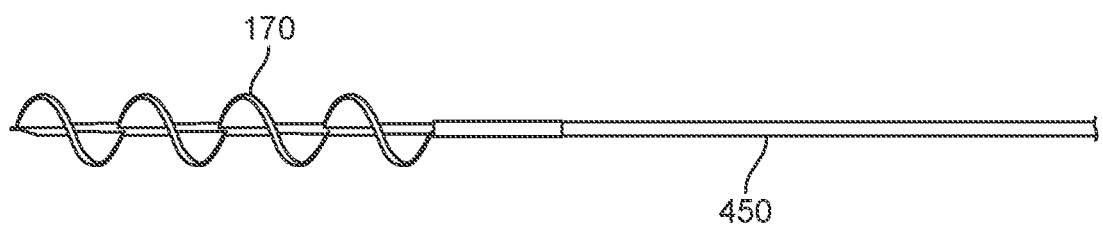

In the embodiment of FIG. 6B, another variation is shown where the blades 170 are configured into a helical screw configuration which is made as a single element. This embodiment may omit an insertion lumen so that the spiraling needle 171 and blades 170 and not made to be guided over an introducing needle.

Regardless of the blade configuration, the blades along the length of the needle body 450 may have a uniform pitch and diameter while in other variations, the pitch and/or diameter may be varied even between the blades.

Figure 7A:
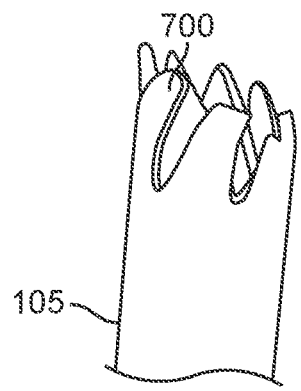
FIGS. 7A to 7C illustrate various shapes of blades of a coring needle included in the turbinate coring device.
Figure 7B:
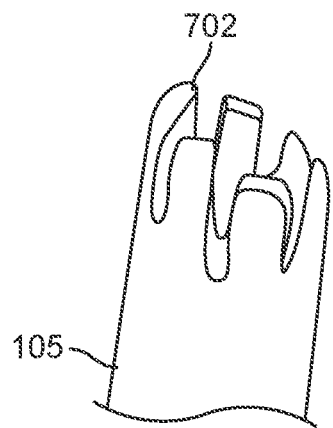
Figure 7C:
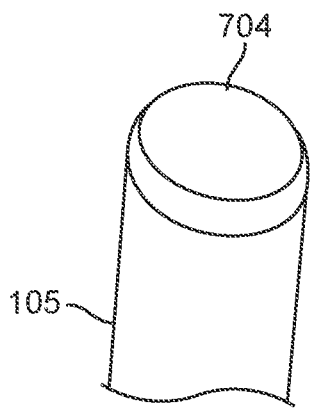

As described previously, the coring needle 105 of the turbinate coring device 100 may include a saw-tooth like arrangement for the blades 107. However, it must be appreciated that the coring blades 107 are in no way restricted to assume the saw-tooth shape. Rather, various shapes of the coring blades are well within the scope of the present disclosure. For example, as shown in FIG. 7A, the configuration 700 depicts a perspective view of an angled saw-tooth configuration for the coring blades. FIG. 7B shows a perspective view of another embodiment where the configuration 702 depicts a straightened saw-tooth configuration, and the configuration 704 shown in FIG. 7C illustrates a continuous edge type blade configuration which may be tapered in a distal direction for the coring blades. The variations are provided only as examples and are not intended to be limiting as to the variations of the blade configurations.

Figure 8A:
FIGS. 8A to 8C illustrate another embodiment of the coring needle having an inner and outer coring member.
Figure 8B:
Figure 8C:
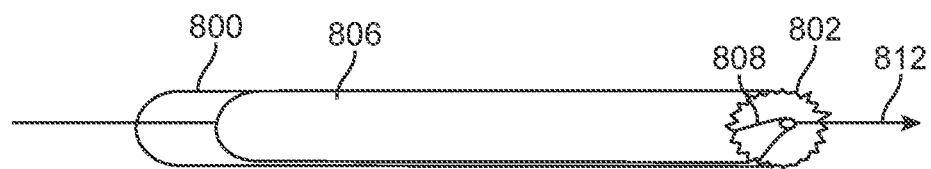

Turning now to the body of the coring needle itself, FIGS. 8A to 8C illustrate perspective views of a variation on the coring needle. The coring needle is illustrated in FIG. 8A having an outer coring member 800 having a tubular cross-section with a cutting blade 802 disposed on the distal end of the member. With this embodiment, the outer coring member 800 may be designed to rotate in a predetermined first direction 804, e.g., clockwise as shown relative to the frame 150. The coring needle may further include an inner coring member 806 which defines a hollow lumen as shown in FIG. 8B which may be configured to rotate in a second direction 810, e.g., counter-clockwise relative to the frame 150, and which is counter to the first direction 804. The inner coring member 806 may have one or more blades 808 disposed on a distal end of the member 806 which is configured to cut through and capture the tissue, as illustrated, when rotated in the second direction 810. Additionally, the inner coring member 806 may have an outer diameter which is less than an inner diameter of the outer coring member 800 to allow for the uninhibited insertion, translation, and rotation of the inner coring member 806 relative to the outer coring member 800. The perspective view of FIG. 8C shows how the inner 806 and outer 800 coring elements may be fit into each other. The assembly may be advanced into the tissue, as illustrated by the direction of movement 812, either alone or over an optional introducing needle, where the outer coring member 800 may be rotated in the first direction 804 and the inner coring member 806 may be rotated in the opposite second direction 810 to facilitate cutting of the tissue, e.g., via a counter-rotating mechanism coupled to the coring members 800, 806. This embodiment may provide a counter force when cutting the tissue; however, the outer coring member 800 or inner coring member 806 may be utilized alone rather than in combination with one another.

Figure 9A:
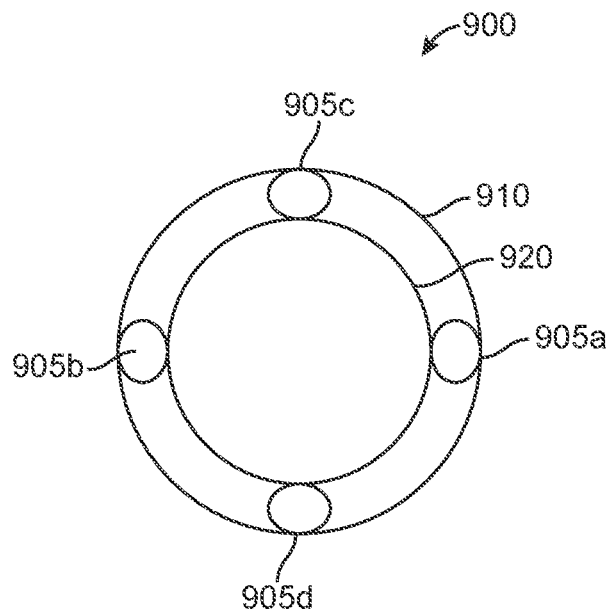
FIGS. 9A and 9B depict exemplary micro-electro-mechanical blades included in a coring needle of the turbinate device in different configurations.
Figure 9B:
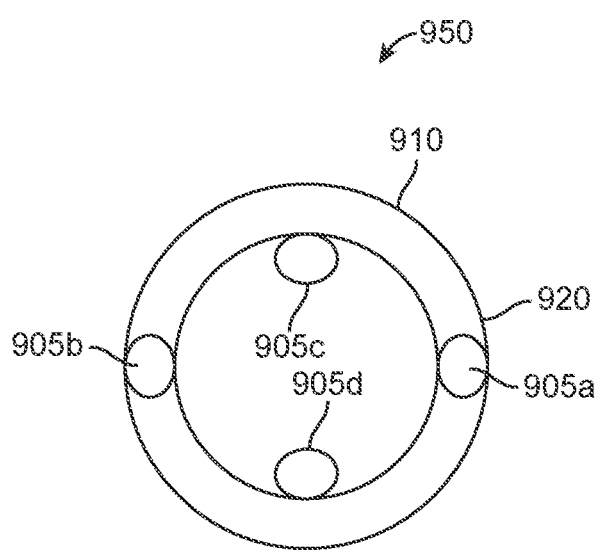

FIGS. 9A and 9B show yet other embodiments of coring needle variations. FIG. 9A, for example, shows an end view of a coring needle 900 having an inner tubular member 920 and an outer tubular member 910. One or more blades 905A, 905B, 905C, 905D may be disposed between the inner and outer tubes 910 and 920, respectively. By one embodiment, each blade of the plurality of blades 905A, 905B, 905C, 905D may comprise, e.g., a micro-electro-mechanical blade. These blades 905A, 905B, 905C, 905D may be of a circular, semi-circular, disk shaped, etc., and the like. Each of the blades 905A, 905B, 905C, 905D may be controlled by a controller (e.g., controller 1050 of FIG. 10). Moreover, while four blades are shown, a single blade or more than four blades may be used. Additionally, the blades are shown uniformly spaced apart from one another within the annular space; however, the blades may be instead placed at non-uniform locations, if desired or needed.

When all the blades 905A, 905B, 905C, 905D are in an inactive state, the blades may be disposed between the inner and the outer tube of the coring needle. However, when activated, as shown in FIG. 9B, one or more of the blades, in this example, blades 905C and 905D, respectively, may be placed into an active state such that the blades 905C, 905D reconfigure or move to become disposed on the inner surface of the inner tube 920 in order to perform the coring process.

Accordingly, by one embodiment, a predetermined number of micro-electro-mechanical blades may be activated, for example, based on a patient type. It is appreciated that the inferior turbinate of different patients may be of different sizes. For instance, the size of the inferior turbinate of an infant may be substantially smaller than that of an adult. Accordingly, when the patient undergoing a turbinate resection is an infant, a first number (e.g., two blades out of four) may be activated. Similarly, if the patient undergoing the turbinate resection is an adult, a second number (e.g., three/four out of four blades) may be activated. Furthermore, by one embodiment, the number of micro-electromechanical blades that may be activated, can be based on an initial scan (e.g., an MRI scan) of the patient's turbinate tissues. Moreover, it must be appreciated that a total number of micro-electro-mechanical blades is in no way restricted to being four. The coring needle of the turbinate device may include any number of micro-electro-mechanical blades.

Figure 10:
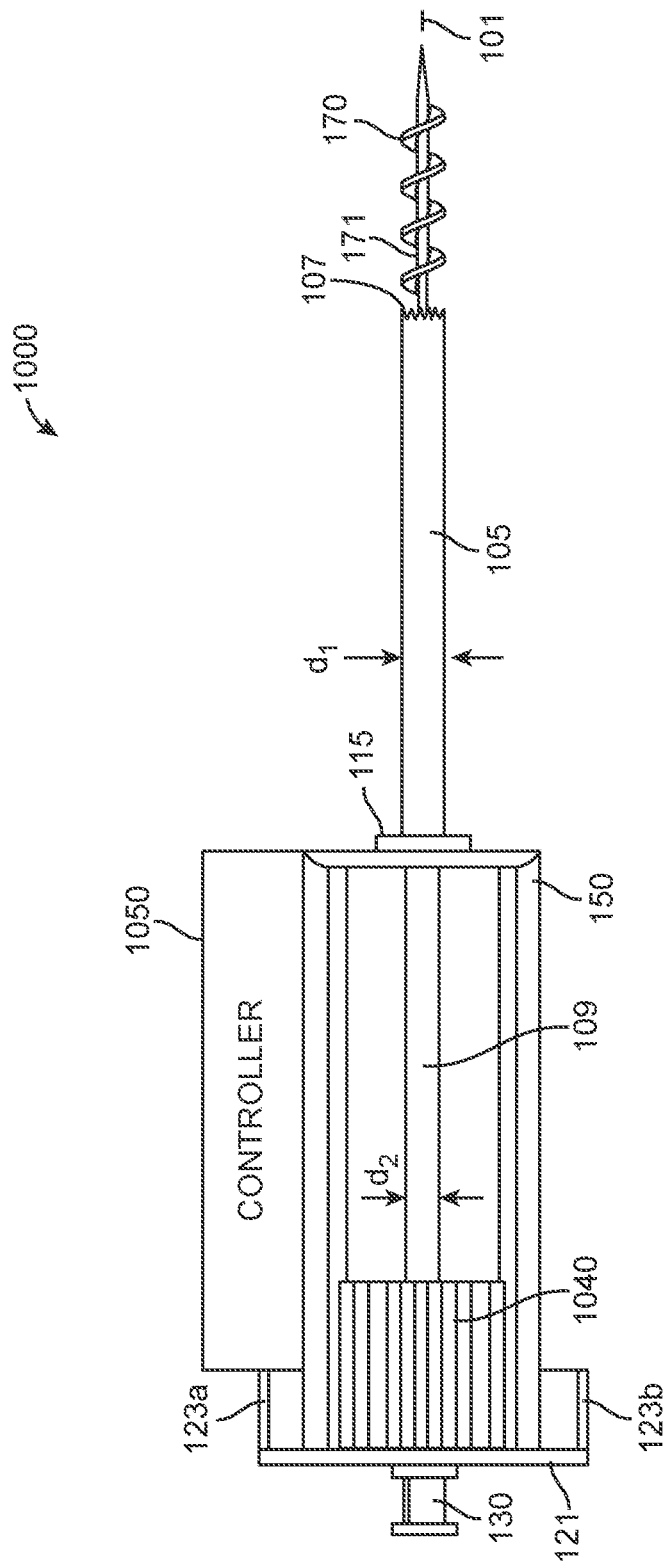
FIG. 10 depicts an exemplary turbinate coring device having a controller.

FIG. 10 depicts an exemplary turbinate coring device 1000 according to another embodiment. The turbinate coring device 1000 is similar to the coring device 100 of FIG.

1, with the exception that the coring device 1000 includes a controller 1050 that controls the operation of the device as described herein.

The parts of the turbinate coring device 1000 as described herein may be identical in functionality while in this embodiment, the turbinate coring device 1000 includes a controller 1050 that controls the operation of a spiraling needle control 1040. As opposed to be manually rotating the control 1040 (as may be done in the turbinate device 100 of FIG. 1), the controller 1050 may include one or more controls, e.g., a pair of push-buttons, which may actuate and control movement of the control 1040 and thereby the spiraling tube 109. Similarly, by depressing actuating the one or more controls, the control 1040 may be configured to move in a distal or proximal manner along the length of the frame 150. The turbinate coring device 1000 may be battery operated and include an actuator mechanism that controls the motion of the control 1040. The controller 1050 may include a processing circuit (described later below) that controls the operation of the turbinate device 1000. Furthermore, the controller 1050 may also include a wired or wireless transmitter and/or receiver (e.g., WiFi, RF, infrared, etc.) that may communicate the location of the control 1040 to a remote computer system. Accordingly, the displacement of the control 1040 may be displayed on a panel, thereby providing a user of the turbinate device (e.g., a surgeon), a pictorial representation of the operation of the turbinate device 1000.

Furthermore, it must be appreciated that although the coring needle 105 is shown to be affixed to the lower end of the frame 150, the coring needle 105 may be controlled in a similar actuator mechanism for insertion and removal purposes, as the spiraling needle control 1040.

Each of the functions of the described embodiments (for instance, the controller 1050 of FIG. 10) may be implemented by one or more processing circuits. A processing circuit includes a programmed processor (for example, processor 1103 in FIG. 11), as a processor includes circuitry. A processing circuit also includes devices such as an application-specific integrated circuit (ASIC) and circuit components that are arranged to perform the recited functions.

Figure 11:
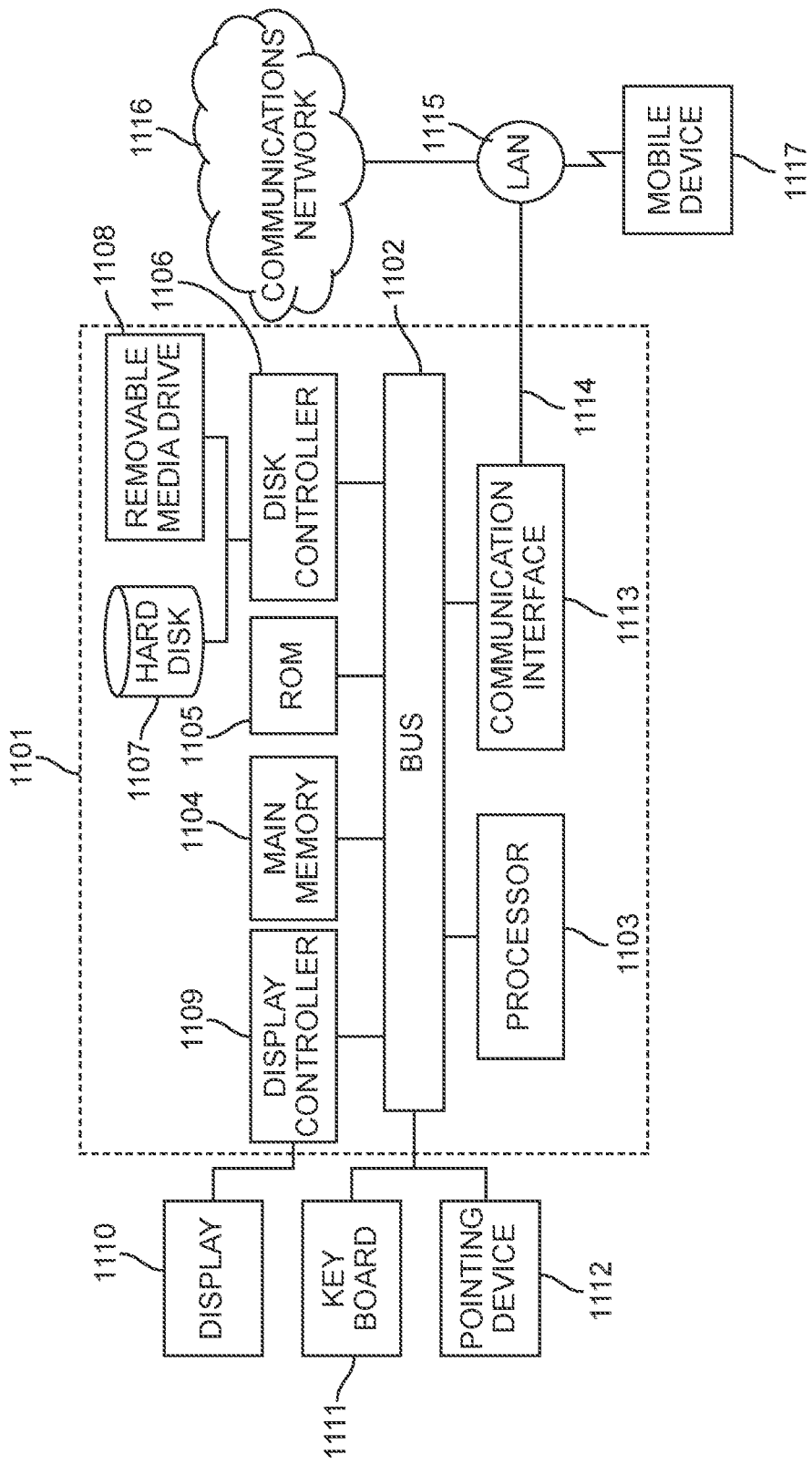
FIG. 11 illustrates a block diagram of a computing device according to one embodiment.

The various features discussed above may be implemented by a computer system (or programmable logic). FIG. 11 illustrates such a computer system 1101. In one embodiment, the computer system 1101 is a particular, special-purpose machine when the processor 1103 is programmed to perform the estimate computations and other functions described herein.

The computer system 1101 includes a disk controller 1106 coupled to the bus 1102 to control one or more storage devices for storing information and instructions, such as a magnetic hard disk 1107, solid state drive, or other storage device, and a removable media drive 1108 (e.g., flash drive, floppy disk drive, read-only compact disc drive, read/write compact disc drive, compact disc jukebox, tape drive, and removable magneto-optical drive, etc.). The storage devices may be added to the computer system 1101 using an appropriate device interface (e.g., small computer system interface (SCSI), integrated device electronics (IDE), enhanced-IDE (E-IDE), direct memory access (DMA), or ultra-DMA).

The computer system 1101 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1101 may also include a display controller 1109 coupled to the bus 1102 to control a display 1110, for displaying information to a computer user. The computer system includes input devices, such as a keyboard 1111 (or other input device), and a pointing device 1112, for interacting with a computer user and providing information to the processor 1103. The pointing device 1112, for example, may be a mouse, a trackball, a finger for a touch screen sensor, or a pointing stick for communicating direction information and command selections to the processor 1103 and for controlling cursor movement on the display 1110.

The processor 1103 executes one or more sequences of one or more instructions contained in a memory, such as the main memory 1104. Such instructions may be read into the main memory 1104 from another computer readable medium, such as a hard disk 1107 or a removable media drive 1108. One or more processors in a multi-processing arrangement may also be employed to execute the sequences of instructions contained in main memory 1104. In alternative embodiments, hard-wired circuitry may be used in place of or in combination with software instructions. Thus, embodiments are not limited to any specific combination of hardware circuitry and software.

As stated above, the computer system 1101 includes at least one computer readable medium or memory for holding instructions programmed according to any of the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes.

Stored on anyone or on a combination of computer readable media, the present disclosure includes software for controlling the computer system 1101, for driving a device or devices for implementing the features of the present disclosure, and for enabling the computer system 1101 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the present disclosure.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1103 for execution. A computer readable medium may take many forms, including but not limited to, non-volatile media or volatile media. Non-volatile media includes, for example, optical, magnetic disks, and magneto-optical disks, such as the hard disk 1107 or the removable media drive 1108. Volatile media includes dynamic memory, such as the main memory 1104. Transmission media, on the contrary, includes coaxial cables, copper wire and fiber optics, including the wires that make up the bus 1102. Transmission media also may also take the form of acoustic or light waves, such as those generated during radio wave and infrared data communications.

Various forms of computer readable media may be involved in carrying out one or more sequences of one or more instructions to processor 1103 for execution. For example, the instructions may initially be carried on a magnetic disk of a remote computer. The remote computer can load the instructions for implementing all or a portion of the present disclosure remotely into a dynamic memory and send the instructions, e.g., over a telephone line using a modem or via any number of wireless communications protocols over cellular networks, satellite, internet, etc. A modem local to the computer system 1101 may receive the data on the telephone line and place the data on the bus 1102. The bus 1102 carries the data to the main memory 1104, from which the processor 1103 retrieves and executes the instructions. The instructions received by the main memory 1104 may optionally be stored on storage device 1107 or 1108 either before or after execution by processor 1103.

The computer system 1101 also includes a communication interface 1113 coupled to the bus 1102. The communication interface 1113 provides a two-way data communication coupling to a network link 1114 that is connected to, for example, a local area network (LAN) 1115, or to another communications network 1116 such as the Internet. For example, the communication interface 1113 may be a network interface card to attach to any packet switched LAN. As another example, the communication interface 1113 may be an integrated services digital network (ISDN) card. Wireless links may also be implemented. In any such implementation, the communication interface 1113 sends and receives electrical, electromagnetic or optical signals that carry digital data streams representing various types of information.

The network link 1114 typically provides data communication through one or more networks to other data devices. For example, the network link 1114 may provide a connection to another computer through a local network 1115 (e.g., a LAN) or through equipment operated by a service provider, which provides communication services through a communications network 1116. The local network 1114 and the communications network 1116 use, for example, electrical, electromagnetic, or optical signals that carry digital data streams, and the associated physical layer (e.g., CAT 5 cable, coaxial cable, optical fiber, etc.). The signals through the various networks and the signals on the network link 1114 and through the communication interface 1113, which carry the digital data to and from the computer system 1101 may be implemented in baseband signals, or carrier wave based signals.

The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1101 can transmit and receive data, including program code, through the network(s) 1115 and 1116, the network link 1114 and the communication interface 1113. Moreover, the network link 1114 may provide a connection through a LAN 1115 to a mobile device 1117 such as a personal digital assistant (PDA) laptop computer, cellular telephone, smartphone, tablet, etc.

Figure 12:
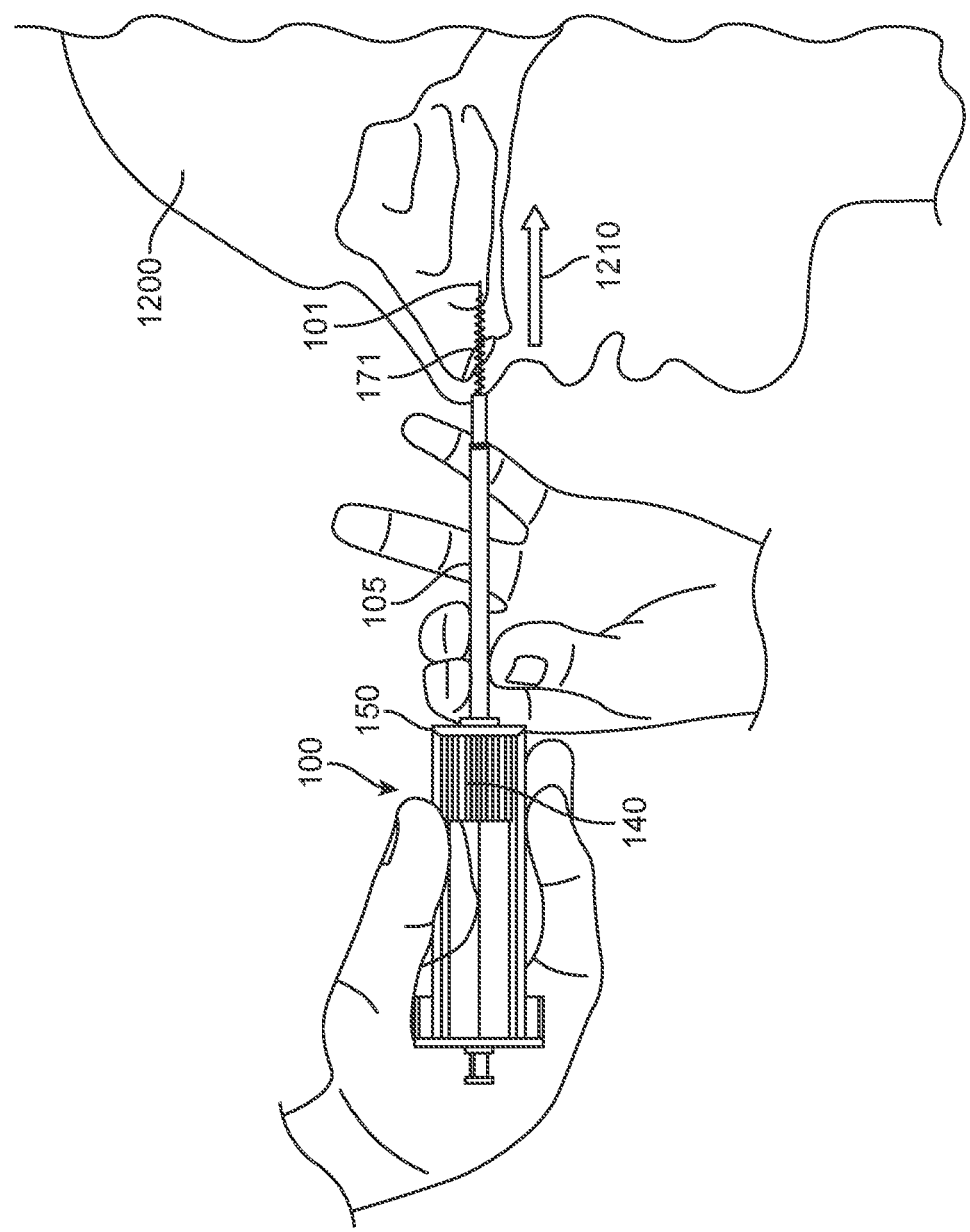
FIG. 12 illustrates a pictorial representation of the turbinate device in operation.

FIG. 12 illustrates a pictorial representation of the turbinate device 100 in operation. The turbinate device 100 is used to resect the turbinate tissue from a patient 1200. As shown, the guiding needle 101 may be initially inserted through the nostril, into the patient's nasal cavity, and then into the tissue (e.g., turbinate tissue) at a desired location of operation. Further, the control 140 may be rotated in a first direction (e.g., a clockwise direction) to project the spiraling needle 171 over or along the guiding needle 101 and distally into the turbinate tissue, as indicated by the direction of movement 1210. Note that the spiraling needle rotates in a coaxial manner over the guiding needle 101.

With the spiraling needle 171 initially inserted into the tissue, the control 140 may be advanced up to a predetermined distance (e.g., using one or more stop mechanisms as described herein) or disposed at an extreme end of the frame 150 of the turbinate coring device 100 such that the spiraling needle 171 is advanced at its extreme position within the turbinate tissue. The spiraling needle 171 provides a template or anchor as well as a counterforce to direct and control the coring needle 105 which may be then advanced over or along the spiraling needle 171. The coring needle 105 with its sharp coring blade or blades may cut the tissue engaged by the spiraling needle 171 as it advances deeper into the turbinate tissue. Accordingly, upon fully advancing the coring needle 105 within the turbinate tissue, an entire predetermined volume or chunk of the turbinate tissue is captured within and resected by the coring needle 105. Upon successful capture of the turbinate tissue, the coring needle can be pulled out of the patient's nose.

It must be appreciated that certain features of the above described embodiments may be performed in combination with features of other embodiments. Furthermore, the turbinate coring device may exclude the guiding needle and only include a combination of the spiraling needle and the coring needle for turbinate tissue resection purposes.

In yet another embodiment, FIGS. 13A to 13D show perspective and detail views of a coring device 1300 utilizing multiple anchoring needles 1308 which are designed to be inserted into the tissue region and define a confined space within the tissue region to be resected. The anchoring needles 1308 are attached and extend in parallel from an anchoring needle base 1306 which is shown in a tubular configuration although alternative shapes may be used. The needles 1308 may extend in parallel with one another and terminate in piercing tips 1310 with the same or different lengths of needles 1308. The needle base 1306 may define a lumen through which a coring needle 1302 having a cutting edge 1304 may be translated. In use, the anchoring needle base 1306 may be advanced distally relative to the coring needle 1302 and frame 150 to advance the anchoring needles 1308, as shown in FIG. 13A, distally into the turbinate tissue. With the anchoring needles 1308 defining the portion of tissue to be resected, the coring needle 1302 may be then advanced distally through the needle base 1306 between the needles 1308, as shown in FIG. 13B, to core the tissue defined. FIG. 13C shows a detail perspective view of the distal end of the piercing tips 1310 and cutting edge 1304 of the coring needle 1302 advanced into proximity of one another when coring the tissue. FIG. 13D shows a perspective exploded assembly view of the individual components.

The forces exerted by the coring needle 1302 during the coring process are countered by the anchoring needles 1308. The coring needle 1302 then can act on the turbinate tissue between the coring needle 1302 and the adjacent anchoring needles 1308, thus limiting the forces exerted on the turbinate as a whole.

The anchoring needles 1308 may be designed to be introduced simultaneously, as shown, or individually. Moreover, while the anchoring needles 1308 are shown as four parallel needles uniformly spaced apart about a circumference of the needle base 1306, the number of needles may be more or less and/or they may be spaced apart from one another in an asymmetric or arbitrary manner, if so desired. Additionally, in other embodiments, the anchoring needles 1308 may be cinched together to increase their purchase of the tissue/bone prior to introduction of the coring needle 1302.

Figure 14A:
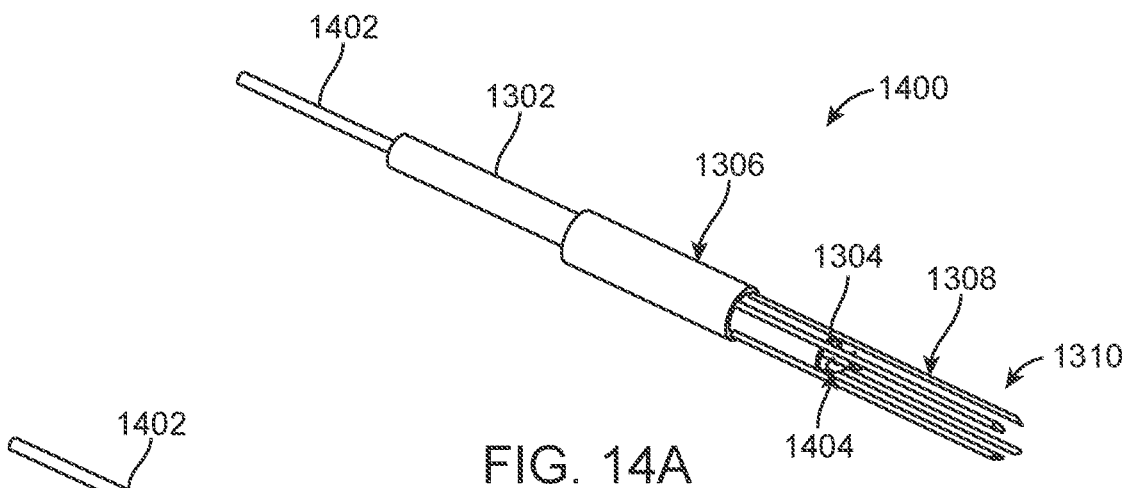
FIGS. 14A to 14E illustrate various perspective views of yet another embodiment of the coring device having multiple anchoring needles and a helically shaped blade.
Figure 14B:
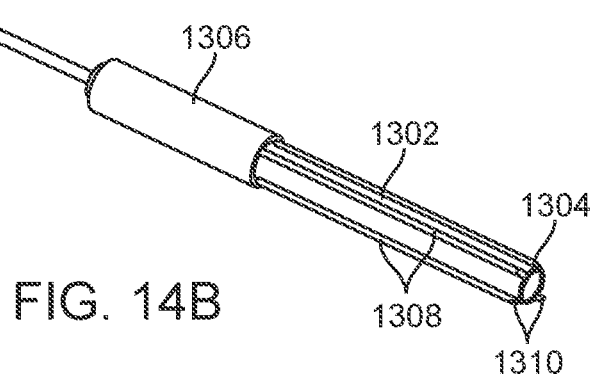
Figure 14C:
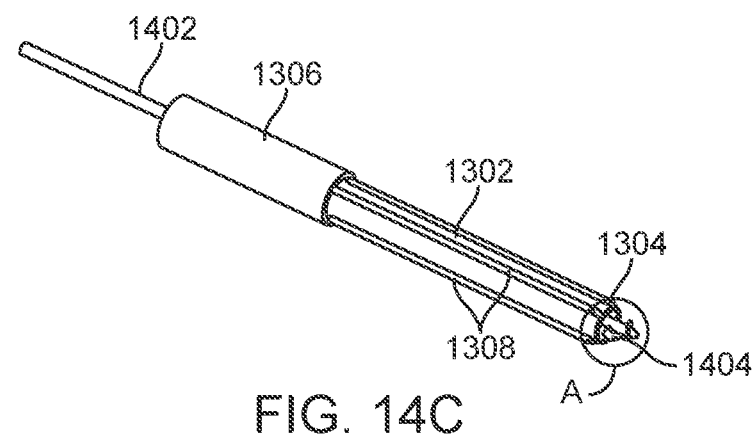
Figure 14D:
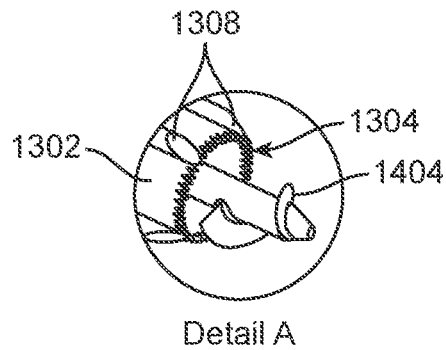
Figure 14E:
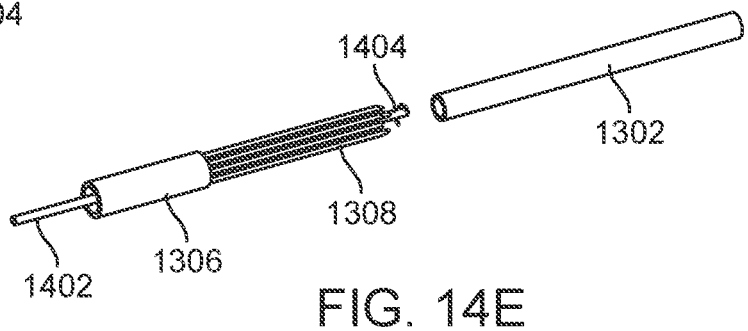

Another embodiment is shown in the perspective views of FIGS. 14A to 14E which illustrates an embodiment 1400 similarly having an anchoring needle base 1306 with multiple anchoring needles 1308 and the coring needle 1302. This embodiment may further incorporate an additional spiraling needle body 1402 (e.g., Trim Helix) having a helically shaped blade 1404 (or any of the blade configurations described herein) to trim the cored turbinate tissue after coring. The spiraling needle body 1402 may also be advanced into the tissue to pre-trim and capture the tissue (as described herein) prior to introduction of the coring needle. As shown in FIG. 14A, the spiraling needle body 1402 may be advanced through the coring needle 1302 and between the anchoring needles 1308 before or after the coring needle 1302 has been advanced, as shown in FIG. 14C. FIG. 14D shows a detail perspective view of the blade 1404 extended distally beyond the piercing tips 1308 and cutting edge 1304 of coring needle 1302. FIG. 14E shows an exploded assembly view of the individual components.

FIGS. 15A to 15F illustrate yet another embodiment 1500 in which a needle base 1502 may incorporate one or more blades 1506 which are configured as individual cutting elements having piercing tips 1504, as shown in FIG. 15C and detail view of FIG. 15B. A sheath 1508 may also be incorporated to slidingly translate over the needle base 1502 and one or more blades 1506, as illustrated in FIG. 15A. Additionally, a coring needle 1302 may also be introduced through the needle base 1502 for coring the tissue, as shown in FIG. 15D and detail view of FIG. 15E. In use, the anchoring blades 1506 may be initially covered by and circumferentially supported through sheath 1508 during initial introduction into proximity of the tissue to be resected. The anchoring blades 1506 may be advanced into the turbinate tissue while cutting the tissue via the blades and the coring needle 1302 may then be introduced through the needle base 1502 and blades 1506 to core the tissue. FIG. 15F illustrates a perspective exploded view of the components of this embodiment.

The anchoring blades 1506 may be created as a stamped array as illustrated, or individual blades. Additionally, the anchoring blades may be designed to be introduced simultaneously, or individually.

FIGS. 16A to 16F show another embodiment 1600 similar to the embodiment above where one or more anchoring blades 1606 having corresponding piercing tips 1604 extending from a needle base 1602, as illustrated in FIGS. 16A and 16B. However, the individual anchoring blades 1606 may incorporate features which facilitate anchoring of the blades 1606 within the tissue. The variation shown in FIGS. 16C and 16D includes barbed features 1608 along at least a portion of the blades 1606. The embodiment 1600 may also be used with the coring needle 1302, as illustrated in FIGS. 16E and 16F.

In yet another embodiment 1700, FIGS. 17A and 17B show a variation where a sheath 1702 having an additional tissue anchor 1704 attached to the distal end of the sheath 1702 may be used in combination with a needle base 1306 having anchoring needles 1308 and coring needle 1302. The tissue anchor 1704 is configured in this variation as a helically-configured anchor, as shown in FIGS. 17A and 17B, for rotating into secure engagement with the tissue region to be resected although in other embodiments, different tissue anchoring configurations may be used.

During use, the tissue anchor 1704 may be introduced into proximity of the tissue region to be treated and advanced into the tissue, e.g., screwed into the anterior surface of the turbinate, either before or after insertion of the anchoring needles 1308. FIG. 17C shows a view of the anchoring needles 1308 advanced distally prior to advancement of the anchor 1704. With the anchor 1704 and needles 1308 secured, the coring needle 1302 may be advanced distally through the anchoring needles 1308, as shown in FIG. 17D. The addition of the anchor 1704 may provide additional stability of the turbinate tissue by engaging and holding the turbinate mucosa anteriorly prior to the coring process. FIG. 17E illustrates a cross-sectional side view showing the relative positioning of the individual components in an assembled configuration and FIG. 17F shows an end view accordingly.

Figure 18A:
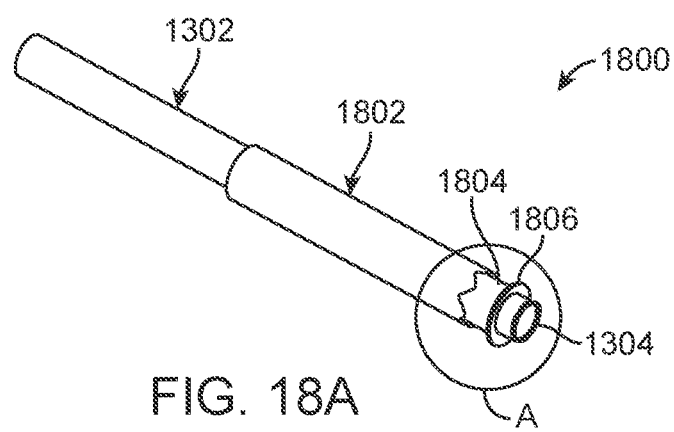
FIGS. 18A to 18G illustrate various perspective views of yet another embodiment of the coring device having a clamping mechanism.
Figure 18B:
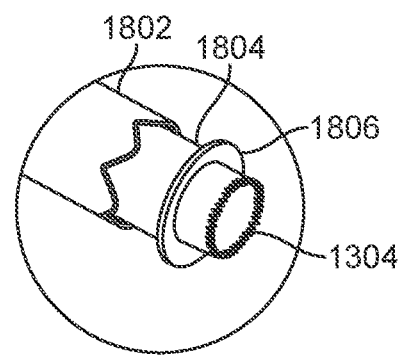
Figure 18C:
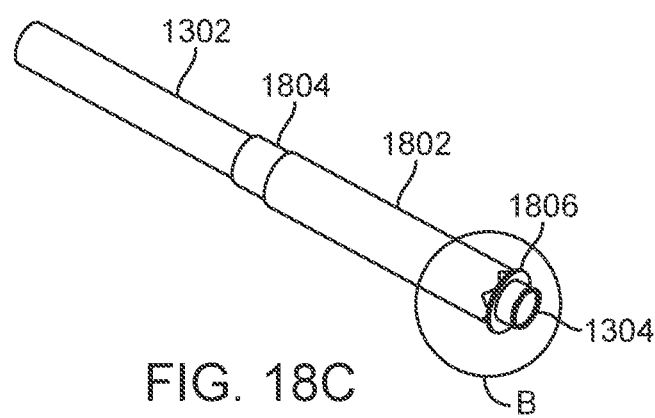
Figure 18D:
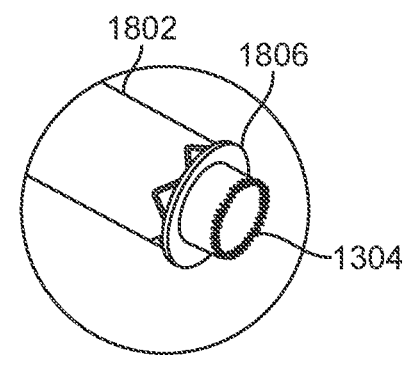
Figure 18E:
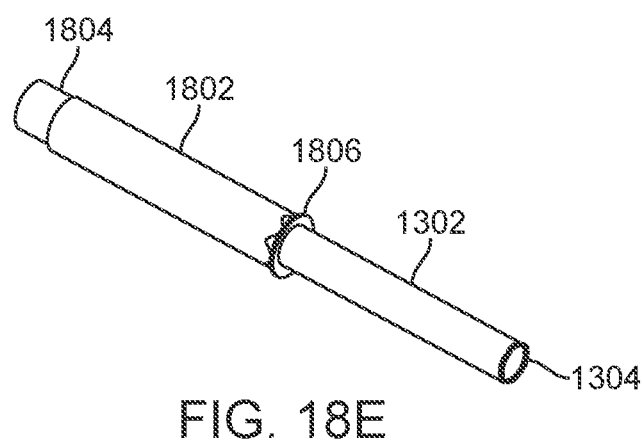
Figure 18F:
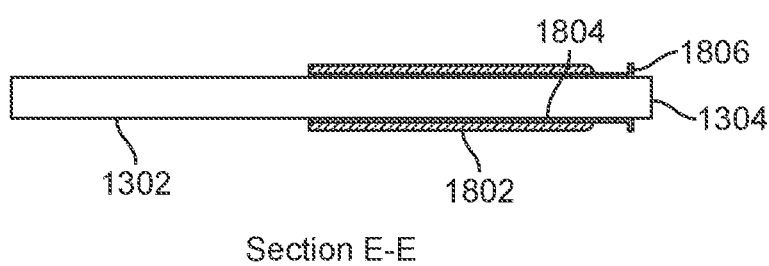
Figure 18G:
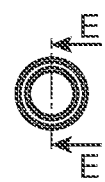

In yet another embodiment, instead of using piercing needles to anchor the tissue region, clamping mechanisms may be used to engage and hold an exterior surface of the tissue region. FIGS. 18A to 18F illustrate an embodiment 1800 which incorporates a sliding clamp mechanism 1802 and a distal clamp mechanism 1806 that may be used to engage and hold the tissue of the anterior surface of the turbinate, e.g., prior to introduction of the coring needle. The distal clamp 1806 may be formed as a shoulder or surface which extends radially from a distal end of a translatable tubular member 1804 while the sliding clamp mechanism 1802 may be formed as a tubular member which defines projections, notched features, or any other mechanism configured to engage tissue, as shown in FIGS. 18A and 18B. The sliding clamp mechanism 1802 may be translatably positioned exterior to the translatable tubular member 1804 so that when the clamp mechanism 1802 and distal clamp 1806 are translated towards one another, tissue may be engaged securely between the two. In use, the device 1800 may be introduced, e.g., in an anterior incision of the turbinate mucosa, and placed submucosally. The sliding clamp 1802 can then be advanced to approximate the distal clamp 1806, as shown in FIGS. 18C and 18D. The distal clamp 1806 and sliding clamp 1802 may thus hold and secure the tissue between them so as to stabilize the anterior turbinate tissue during the coring process. As illustrated in FIG. 18E, the coring needle 1302 may then be advanced as shown to resect the tissue. FIGS. 18F and 18G illustrate cross-sectional side and end views to illustrate the relative positioning of the individual components relative to one another.

Figure 19A:
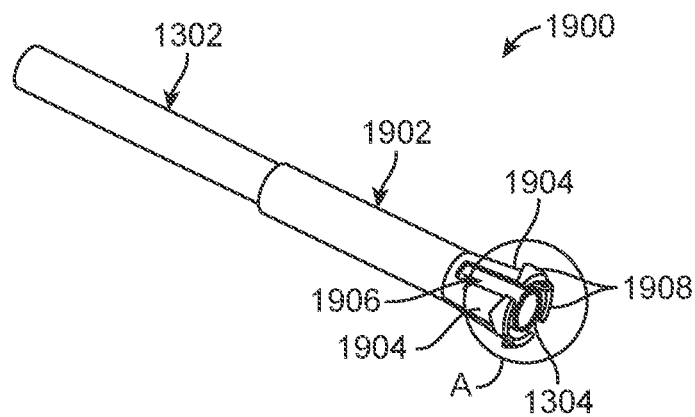
FIGS. 19A to 19C illustrate various perspective views of yet another embodiment of the coring device having radially extending anchoring members.
Figure 19B:
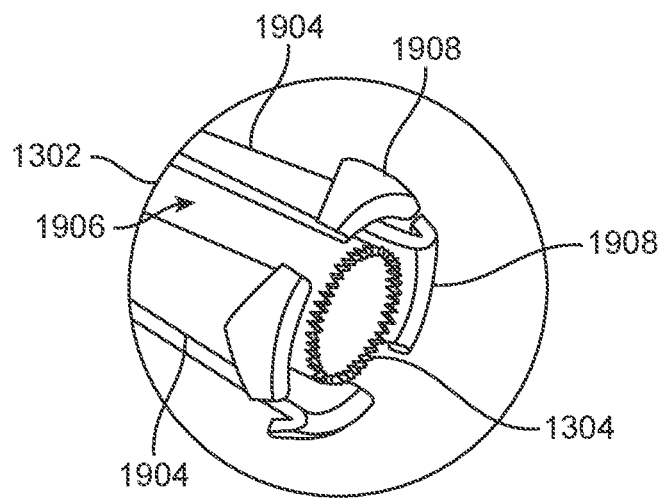
Figure 19C:
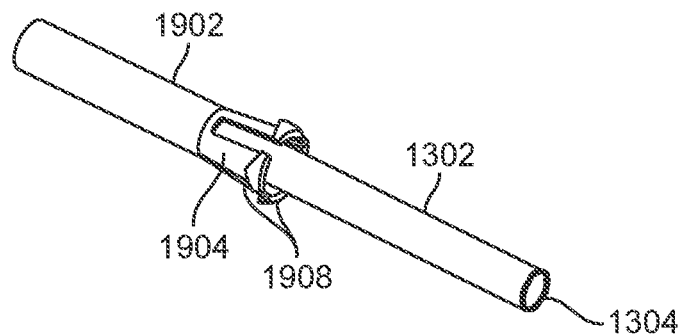

FIGS. 19A to 19C show yet another embodiment 1900 in which a distal flex anchor 1908 may be introduced submucosally prior to the coring process. The distal anchor 1908 may be configured to have projections which extend radially from corresponding members 1904 which extend longitudinally from a sheath member 1902 and define slots or grooves 1906 between each of the adjacent members 1904, as shown in FIGS. 19A and 19B. While four members 1904 are shown, this is intended to be illustrative and other variations may incorporate fewer than four or more than four members. The members 1904 may be biased to flare or extend radially away from the sheath member 1902 such that the distal anchor 1908 (which may incorporate tissue engagement features such as barbs, projections, etc.) may be pressed inwards towards the interior of the device during distal advancement into the tissue but when retracted, may extend radially so that the distal anchor 1908 buried or engaged in the tissue, e.g., anterior turbinate tissue, and hold that tissue during the advancement of the coring needle 1302, as illustrated in FIG. 19C.

Figure 20:
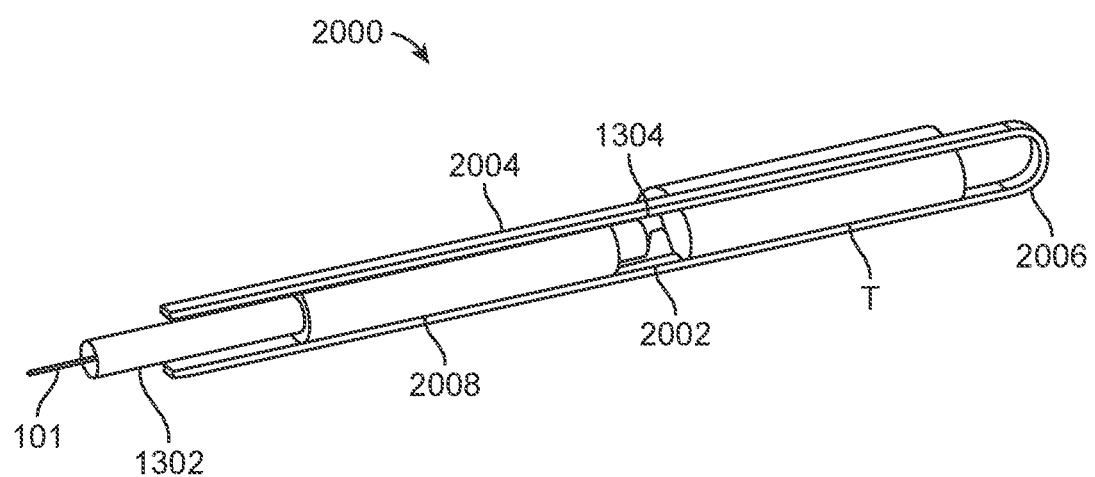
FIG. 20 illustrates a perspective view of yet another embodiment of the coring device having clamping arms that hold each side of the turbinate tissue and optionally envelop the distal end of the turbinate.

In yet another embodiment 2000, FIG. 20 shows a perspective view of a configuration for securing the tissue, e.g., turbinate tissue, externally along an outer surface of the tissue to allow the coring process. An external clamping mechanism 2006 may be comprised of wire, ribbon, or other structural members 2002 shaped with an atraumatic looped or closed distal end, as shown, or into an opened configuration. This clamping mechanism 2006 may extend distally over an optional anchoring base 2008, e.g., configured as a tubular member, so that a distal end of the anchoring base 2008 and a proximal end of the clamping mechanism 2006 present a region to engage and capture the tissue T to be cored. The figure shows an optional introducing needle 101.

The clamping mechanism 2006 may be advanced over the tissue the tissue region to be resected and with the anchoring base 2008 and coring needle 1302 retracted relative to the clamping mechanism 2006, the mechanism 2006 may be positioned over the external surface of the tissue and into proximity of the tissue region for resection. The anchoring base 2008 may be advanced into contact against a proximal region of the tissue T while the distal region of the tissue is retained by the clamping mechanism 2006. The coring needle 1302 may be advanced distally through a lumen defined by the anchoring base 2008 and into the engaged turbinate tissue while the clamping mechanism 2006 provides a counter-force for the coring procedure.

In yet another embodiment, FIGS. 21A to 21D show another variation 2100 which utilize clamp guides 2106A, 2106B which are rails or structural features that extend distally from a guide body 2102 and are positioned in place on the opposite outer surfaces of the tissue, e.g., turbinate tissue. The clamp guides 2106A, 2106B are illustrated as two apposed features although more than two guides may be used in other variations. Corresponding clamp members 2104A, 2104B which extend from a clamp lock 2110 can be advanced over the guides 2106A, 2106B, as shown in FIG. 21A, along the side surfaces of the turbinate tissues such that the clamp members 2104A, 2104B slide along the guides 2106A, 2106B, as shown in FIGS. 21B and 21C, and into apposition over the tissue which may be held within the defined clamping region 2116. In other variations, the clamp members 2104A, 2104B may be utilized without the use of the guides 2106A, 2106B.

The guide body 2102 can be held by the operator as some elements are advanced and the distal ends of the guides 2106A, 2106B may also define features such as projections 2118 which may pierce at least partially into the exterior surface of the tissue. Other features may include teeth that impact or penetrate the mucosa of the turbinate, or may include an indentation at the distal end to hold onto the turbinate tissue.

The guide body 2102 may also be designed to lock onto a scope 2112, e.g., endoscope, such that the scope distal end 2114 may be positioned to extend between the clamp members 2104A, 2104B and used to visualize the placement of the clamp members 2104A, 2104B and may also be used to visualize the coring process before, during, or after the coring needle 1302 is advanced, as shown in FIG. 21D. The clamp lock 2110 may be designed to lock the clamp members 2104A, 2104B in position relative to the guide body 2102. The clamp lock 2110 may be designed to place a force on the clamps or move the clamps such that the clamps will grasp the turbinate tissue in-between them. In other variations, a helical screw (as described herein), may also be used with the embodiment described to excise the tissue.

Figure 22A:
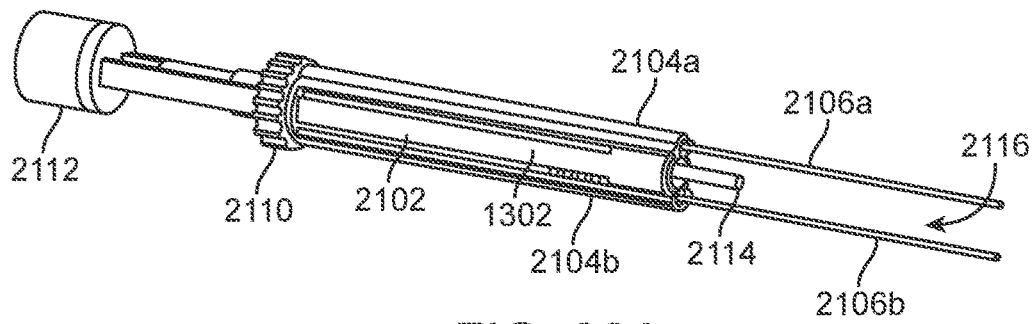
FIGS. 22A to 22E illustrate various perspective views of yet another embodiment of the coring device incorporating a locking feature for clamping the device upon the tissue region of interest.
Figure 22B:
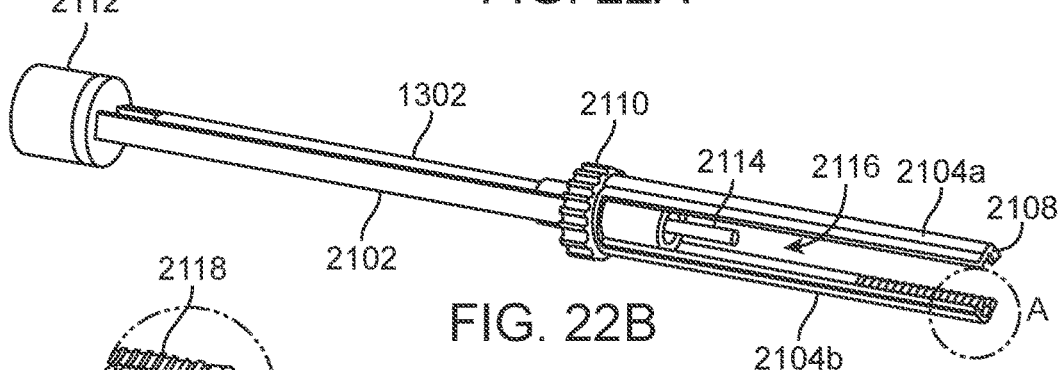
Figure 22C:
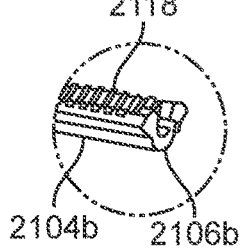

Another example is illustrated in the perspective views of FIGS. 22A to 22E which show the guide body 2102, clamp members 2104A, 2104B, and guides 2106A, 2106B extended, e.g., within the tissue region of interest. Once the clamp members 2104A, 2104B have been advanced distally over the guides 2106A, 2106B, as shown in FIG. 22B, the tissue to be treated is retained within the defined clamping region 2116 between the clamp members 2104A, 2104B.

Figure 22D:
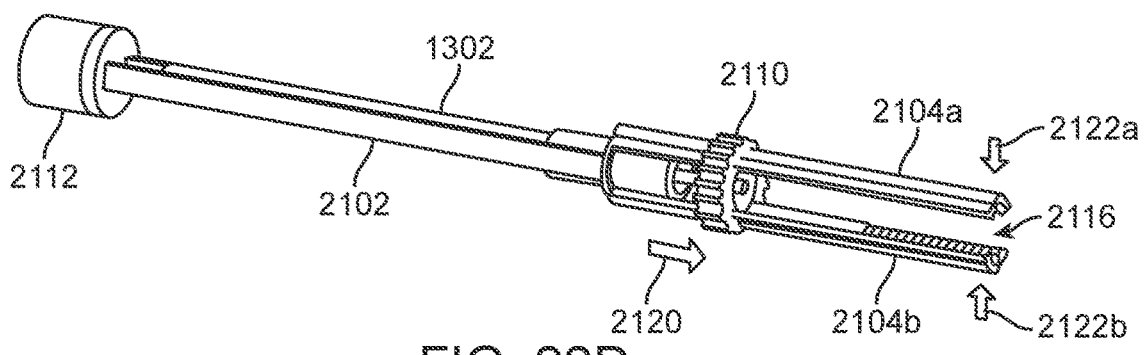

To increase the retention force upon the tissue within clamping region 2116, the clamp lock 2110 may be advanced distally, as indicated by the direction of travel 2120 shown in FIG. 22D, over the clamp members 2104A, 2104B while the clamp members 2104A, 2104B and tissue are held stationary. The clamp lock 2110 may be advanced along the clamp members 2104A, 2104B by sliding the lock distally. Alternatively, the lock 2110 may be rotated in a first direction about the clamp members 2104A, 2104B to advance distally and rotated in a second opposite direction to retract the lock 2110 proximally so as to loosen the clamp members 2104A, 2104B relative to the tissue. An outer surface of the clamp members 2104A, 2104B may define a gradually tapered surface so that distal positioning of the lock 2110 approximates the clamp members 2104A, 2104B towards one another, as indicated by the direction of approximation 2122A, 2122B of each respective clamp member 2104A, 2104B shown.

Figure 22E:
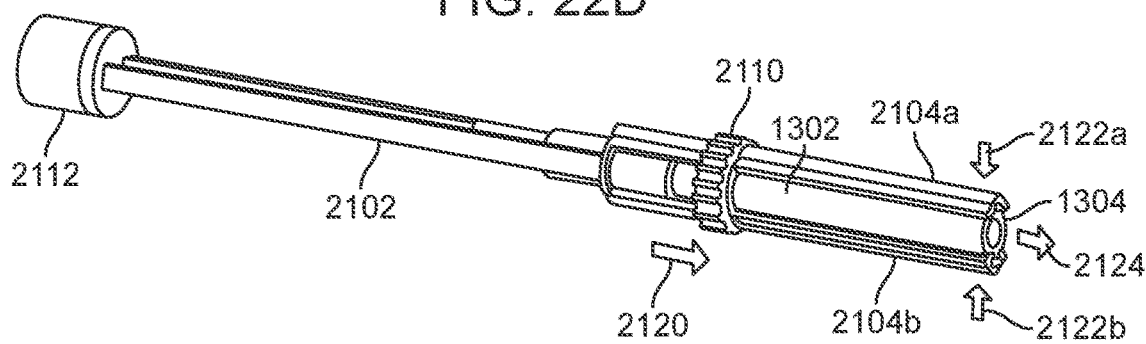

Once the clamp members 2104A, 2104B are sufficiently approximated and locked into position by clamp lock 2110 against the tissue, coring needle 1302 may be advanced distally and into the engaged turbinate tissue, as shown by the direction of travel 2124 in FIG. 22E.

Figure 23:
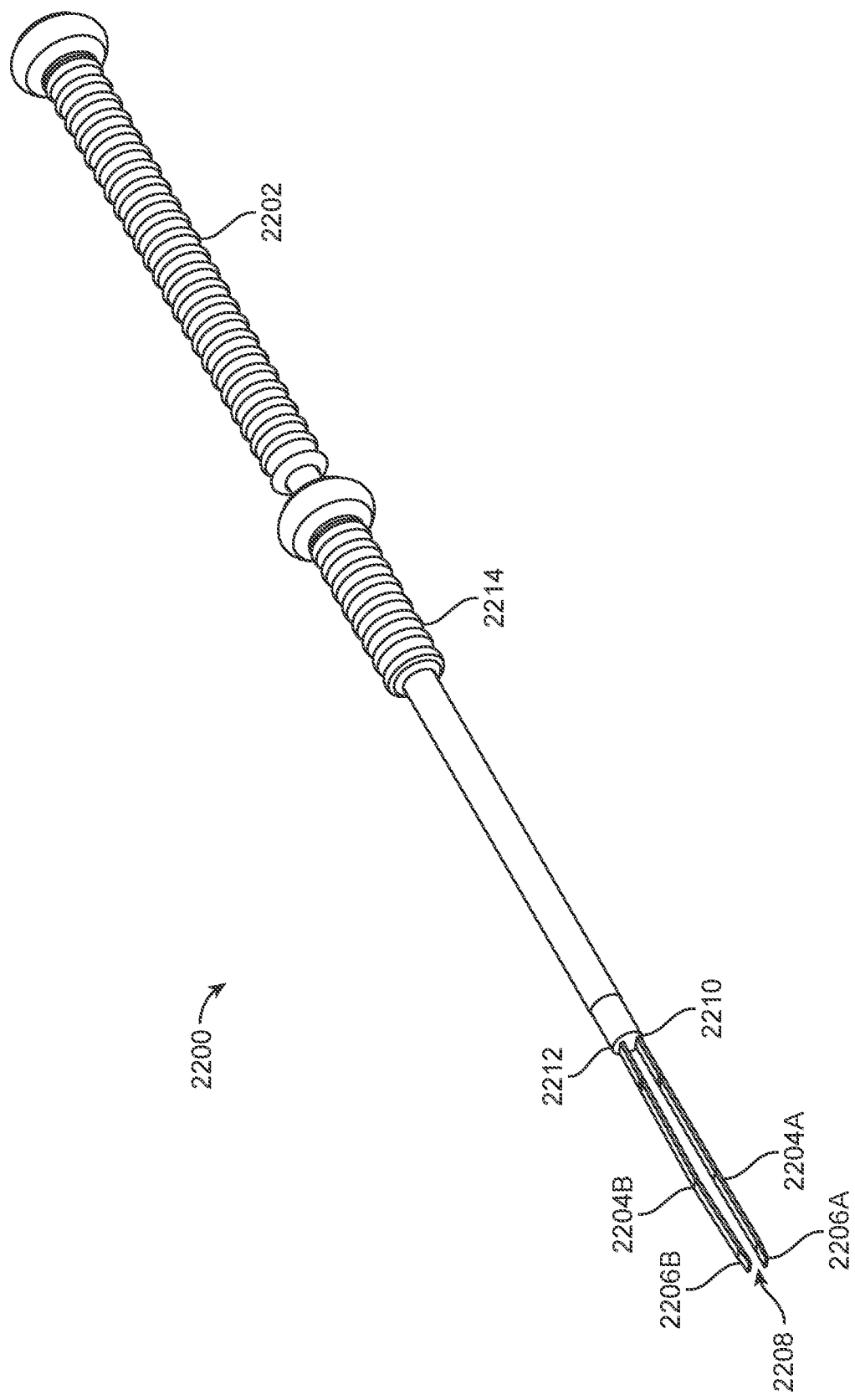
FIG. 23 illustrates a perspective view of an assembly in which the clamp members may be guided into or over upon a portion of the turbinate tissue to be removed.

In yet another variation, FIG. 23 shows a perspective view of an assembly 2200 in which the clamp members may not only be clamped upon an outer surface of the tissue but they may be pierced into a portion of the turbinate tissue to be removed. As described, the clamp members may not only be used for clamping upon an outer surface of the tissue, but they may also pierce directly into the tissue for clamping, holding, or maintaining the tissue from within the tissue region as well. The embodiment shown may include a handle portion 2202 from which an elongate member may extend. At least two apposed clamp members 2204A, 2204B may extend distally from a distal end of the elongate member and terminate in respective piercing tips 2206A, 2206B while defining a clamping region 2208 between the two extending clamp members 2204A, 2204B. The clamp members 2204A, 2204B may also each define a curvature or angle so that the members 2204A, 2204B extend distally with a slight radial curvature or angle away from one another. As described herein, the curvature or angle along the clamp members may be embodied in any number of different configurations and thus the curvature or angle may be located along any portion of the clamp members so long as the clamp members are urged towards one another as the coring needle (or separate elongate element) is advanced over the clamp members.

A coring needle 2210 having a distal cutting edge 2212 may be slidably positioned along the device and positioned proximally of the clamp members 2204A, 2204B. During use, the coring needle 2210 may be positioned proximally of the clamp members 2204A, 2204B as the clamp members 2204A, 2204B are advanced into, e.g., the nasal cavity and directly into the turbinate tissue region of interest for treatment. The clamp members 2204A, 2204B may pierce into the tissue and once suitably advanced a sufficient distance, a position of the clamp members 2204A, 2204B may be maintained relative to the tissue while the coring needle 2210 may be advanced distally over the clamp members 2204A, 2204B by pushing the coring needle handle 2214. As the cutting edge 2212 is advanced distally, the coring needle 2210 may contact against and urge the clamp members 2204A, 2204B towards one another due to their radial curvature or angle so that the tissue positioned within the clamping region 2208 between the clamp members 2204A, 2204B are squeezed or secured to provide better capture or purchase of the tissue as well as providing a counter force as the cutting edge 2212 cuts the surrounding tissue.

Figure 24A:
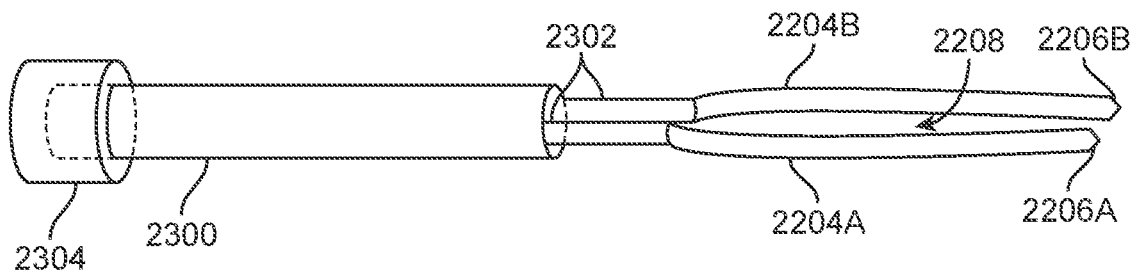
FIGS. 24A to 24C illustrate perspective views of examples of the clamp members and coring needle.
Figure 24B:
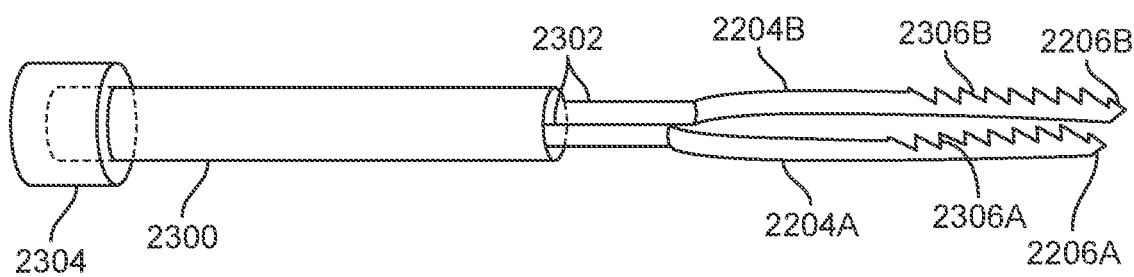

FIG. 24A shows a perspective view of one example of the clamp members 2204A, 2204B connected 2302 at their proximal ends and extend from an elongate member 2300 with the coring needle removed for clarity purposes only. A handle portion 2304 is also shown at the proximal end of the elongate member 2300. The clamp members 2204A, 2204B may be seen extending distally and defining a radially outward curvature or angle relative to the elongate member 2300 as the members 2204A, 2204B extend and terminate at their respective piercing tips 2206A, 2206B. FIG. 24B shows another variation of the clamp members 2204A, 2204B including one or more features or projections 2306A, 2306B defined along the clamp members 2204A, 2204B which improve gripping or anchoring of the members 2204A, 2204B against tissue. These features or projections 2306A, 2306B may include any number of mechanisms such as teeth, barbs, mesh, etc.

Figure 24C:
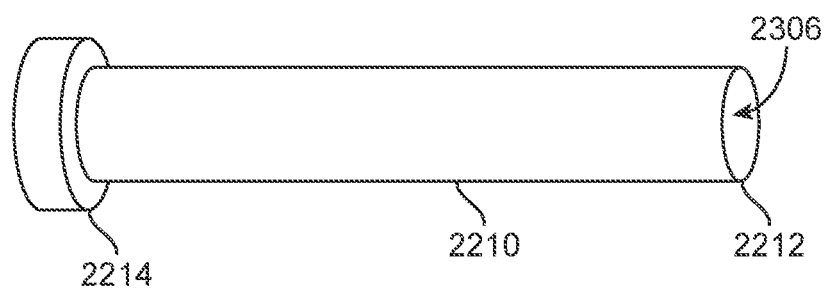

FIG. 24C shows a perspective view of one variation of the coring needle having an elongate tubular body 2210, handle portion 2214 located along a proximal end of the device, cutting edge 2212, and a lumen 2306 within which the captured tissue may be enveloped.

FIGS. 25A and 25B show exemplary perspective views of one variation of the device in use. As shown, the clamp members 2204A, 2204B may be advanced within, e.g., the nasal passage of a subject and the tips 2206A, 2206B may be inserted into a turbinate tissue T region of interest to be reduced, as shown in FIG. 25A. The clamp members 2204A, 2204B may be advanced within the tissue to a desired distance and the coring needle 2210 may be then advanced over the elongate member 2300 and over the clamp members 2204A, 2204B into the tissue. As the coring needle 2210 is advanced, the needle 2210 may be optionally rotated to facilitate cutting of the tissue by the cutting edge 2212. Also, due to the outward radial curvature or angle of the clamp members 2204A, 2204B, at least a portion of the clamp members 2204A, 2204B may protrude or extend past the inner diameter of the coring needle 2210 so that as the coring needle 2210 is advanced distally, its inner surface may contact the outer surfaces of the curved or angled portion of the clamp members 2204A, 2204B such that the members are urged or forced towards one another to further clamp upon the tissue 2400 held between the clamp members 2204A, 2204B within the clamping region 2208, as shown in FIG. 25B. As the coring needle 2210 is further advanced over the tissue 2400 held between the clamp members 2204A, 2204B, the cutting edge 2212 may cut the remainder of the tissue 2400 now fully enclosed within the lumen 2306 of the coring needle 2210 and the assembly and cored tissue 2400 may be removed from the turbinate tissue T.

Figure 26A:
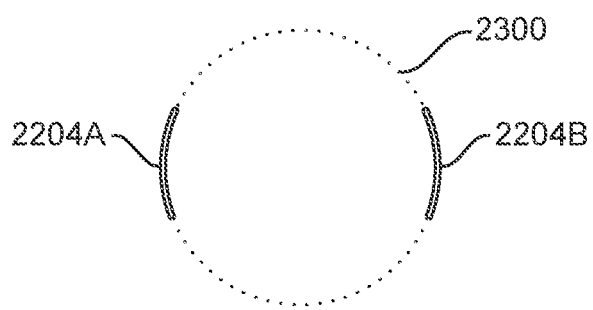
FIGS. 26A to 26C illustrate examples in the end views to illustrate the relative motion of the clamp members.
Figure 26B:
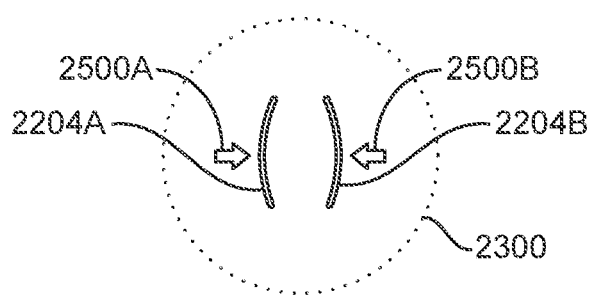
Figure 26C:
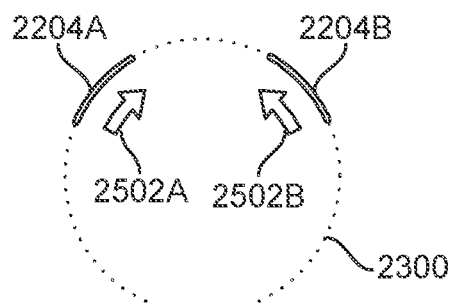

To further illustrate the clamping motion of the clamp members when the coring needle is advanced distally over the members, FIGS. 26A to 26C show examples in the end views to illustrate the relative motion. FIG. 26A shows an end view of the elongate member 2300 and the representative end views of clamp members 2204A, 2204B. The members are shown as having a curved cross-sectional shape; however, the clamp members 2204A, 2204B are illustrated as such for illustrative purposes and the clamp members 2204A, 2204B may instead have any number of cross-sectional shapes.

During initial insertion of the clamp members 2204A, 2204B into the tissue, the clamp members 2204A, 2204B may remain in a relatively straightened configuration. The curve or angle along the lengths of the clamp members 2204A, 2204B are not shown in these examples for clarity purposes only. Once the clamp members 2204A, 2204B have been suitably inserted into and positioned within the tissue region, the coring needle may be advanced distally relative to the clamp members 2204A, 2204B such that the members are urged towards one another against the tissue clamped between, as indicated by the respective arrows 2500A, 2500B, as shown in the end view of FIG. 26B. Alternatively, the clamp members 2204A, 2204B may instead be moved tangentially towards one another, as indicated by respective arrows 2502A, 2502B so that the tissue becomes pinched between the clamp members, as shown in FIG. 26C.

Figure 27A:
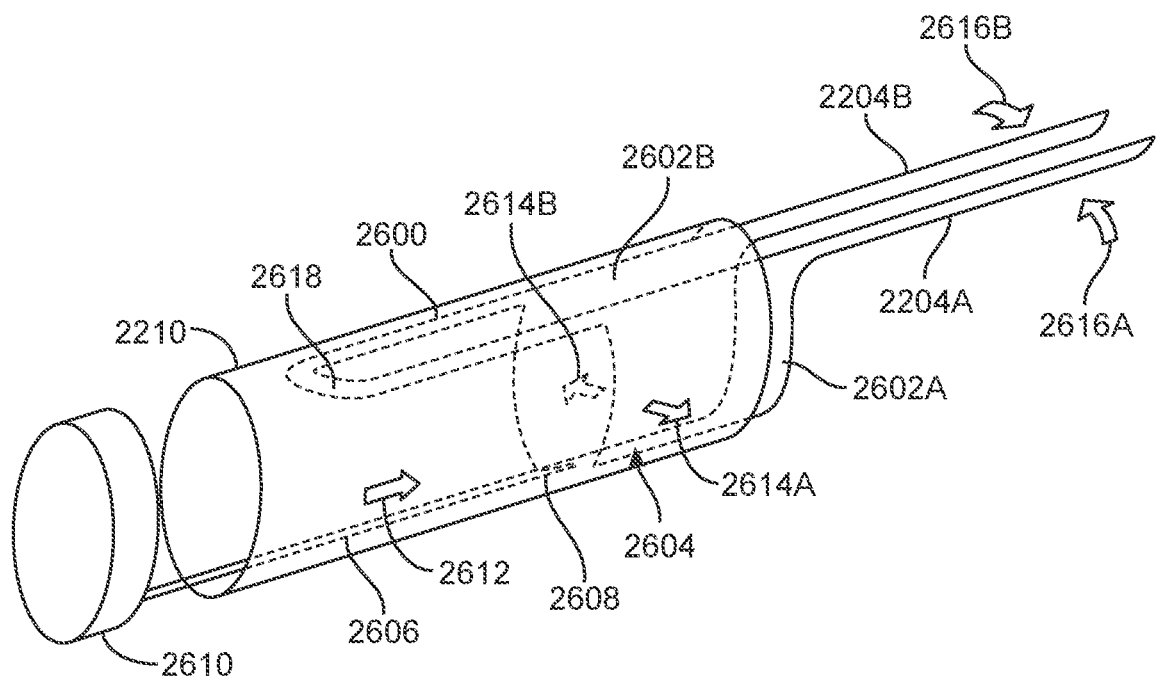
FIGS. 27A and 27B illustrate a perspective and detail view of an assembly which is configured to tangentially pinch or hold upon the tissue between the clamp members.

In another variation, FIG. 27A shows a perspective view of an assembly 2600 which is configured to tangentially pinch or hold upon the tissue between the clamp members 2204A, 2204B. The coring needle 2210 may be shown to surround a proximal portion of the clamp members 2204A, 2204B which extend distally and are coupled to one another at their proximal ends via a connecting member 2618. Each of the clamp members 2204A, 2204B may have a respective leveraging member 2602A, 2602B which is connected or otherwise coupled or in communication with the clamp members 2204A, 2204B and extends circumferentially to define a gap opposite to the connection location. The leveraging members 2602A, 2602B may form an interface surface 2604 which may be tapered along the formed gap. A plunger assembly having a handle portion 2610 and a plunger arm 2606 extending distally and terminating at distal end may be slidably positioned along the assembly in parallel with the formed gap opposite to the connecting member 2618 and clamp members 2204A, 2204B.

Figure 27B:
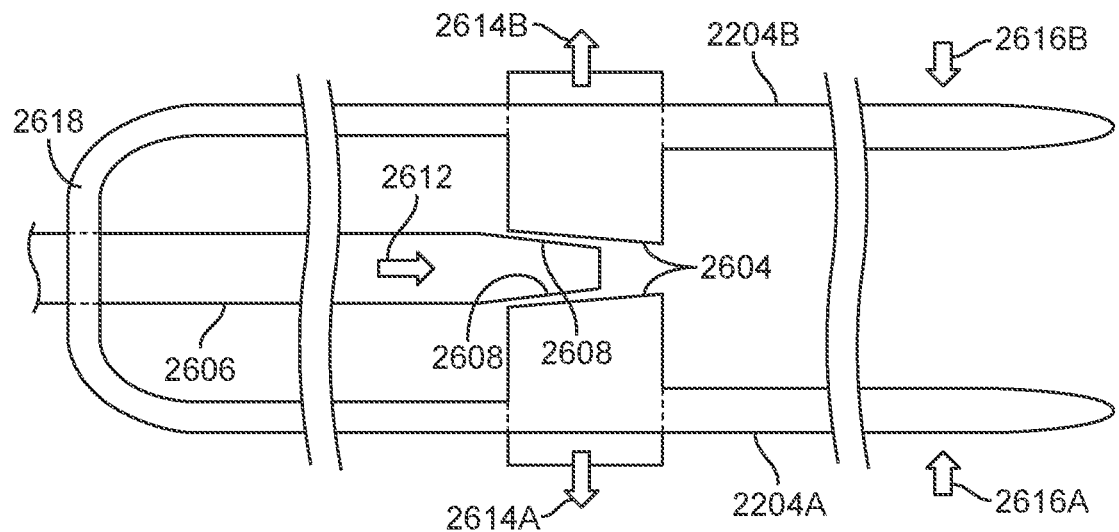

As the plunger is moved distally, as indicated by the arrow 2612, the distal end of the plunger arm 2606 may be moved into the gap defined by leveraging members 2602A, 2602B, as shown in the detail top view of FIG. 27B. The distal end of the plunger arm 2606 may define tapered interface surfaces 2608 which are tapered in an opposite configuration relative to the interface surfaces 2604 defined by the leveraging members 2602A, 2602B such that when the plunger arm 2606 is advanced, the plunger arm interface surfaces 2608 may contact the interface surfaces 2604 and force the adjacent portion of each leveraging member 2602A, 2602B away from one another. As the adjacent portions of members 2602A, 2602B are moved away, as indicated by respective arrows 2614A, 2614B, the leveraging members 2602A, 2602B may be forced to rotate circumferentially when constrained within a lumen so that the upper portion of the leveraging members 2602A, 2602B are forced to move towards one another in a tangential arc as they pivot about connecting member 2618. In turn, the clamp members 2204A, 2204B may also be forced to move towards one another tangentially, as indicated by arrows 2616A, 2616B, so that they pinch or further clamp upon tissue positioned between.

Figure 28A:
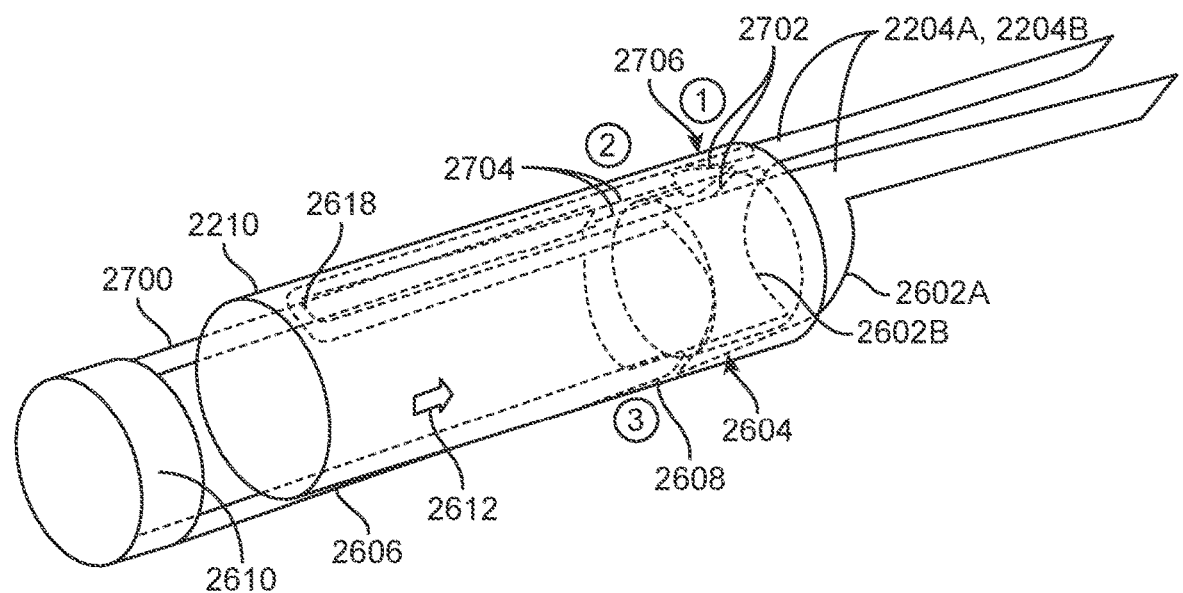
FIG. 28A illustrates perspective view of another variation which includes a second plunger arm.
Figure 28B:
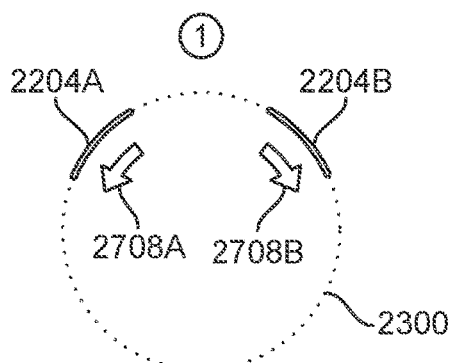
FIGS. 28B to 28D illustrate examples in the end views to illustrate the relative motion of the clamp members.
Figure 28C:
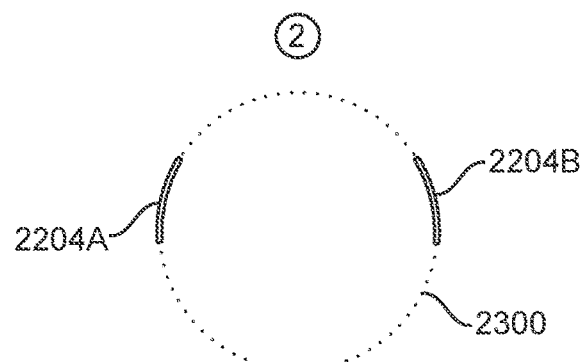
Figure 28D:
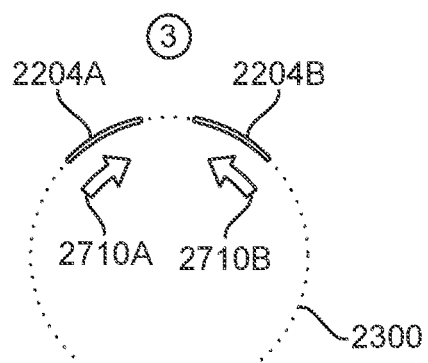

Another variation configured to provide an additional clamping force upon tissue is shown in the perspective view of FIG. 28A and the corresponding detail end views of FIGS. 28B to 28D. The variation shown is similar to the previous variation but includes a second plunger arm 2700 which extends from the handle portion 2610 and is positioned opposite to the plunger arm 2606. The distal end of the second plunger arm 2700 may include a tapered portion 2702 positioned at a distal end of the arm 2700 and a reduced portion 2704 positioned proximal of the tapered portion 2702 along the arm 2700. Additionally, the upper portion of the leveraging member 2602A, 2602B adjacent to where the clamp members 2204A, 2204B extend may also define a tapered interface 2706 corresponding to the tapered portion 2702 of second plunger arm 2700.

The tapered portion 2702 of second plunger arm 2700 may be positioned distal to the interface surface 2608 of the first plunger arm 2606 such that the interface surface 2608 is either aligned with or proximal to the reduced portion 2704 of the second plunger arm 2700. The staggering or relative positioning of these features may be adjusted so that the resulting movement of the clamp members 2204A, 2204B may be sequenced accordingly depending upon the advancement of the handle portion 2610.

Prior to the clamp members 2204A, 2204B being inserted into the tissue, the handle portion 2610 may be advanced to a first position, indicated by the detail view of FIG. 28B, where the tapered portion 2702 of second plunger arm 2700 may engage with the tapered interface 2706 to distract the clamp members 2204A, 2204B away from one another, as indicated by arrows 2708A, 2708B, until the clamp members 2204A, 2204B are repositioned into a distracted configuration, as shown in the end view of FIG. 28C. The clamp members 2204A, 2204B may then be advanced into the tissue region of interest to a desired depth.

From this second position, the handle portion 2610 may be advanced further distally until the tapered portion 2702 is translated distally past the tapered interface 2706 and the reduced portion 2704 is reached allowing the tapered interface 2706 to reposition back into its relaxed state such that the tissue positioned between the clamp members 2204A, 2204B are now clamped. Further advancement of the handle portion 2610 may then urge the tapered interface surfaces 2608 of plunger arm 2606 to then engage the interface surface 2604 to further cause the clamp members 2204A, 2204B to further move tangentially towards one another, as indicated by arrows 2710A, 2710B in FIG. 28D, to further clamp upon the retained tissue region.

Figure 29A:
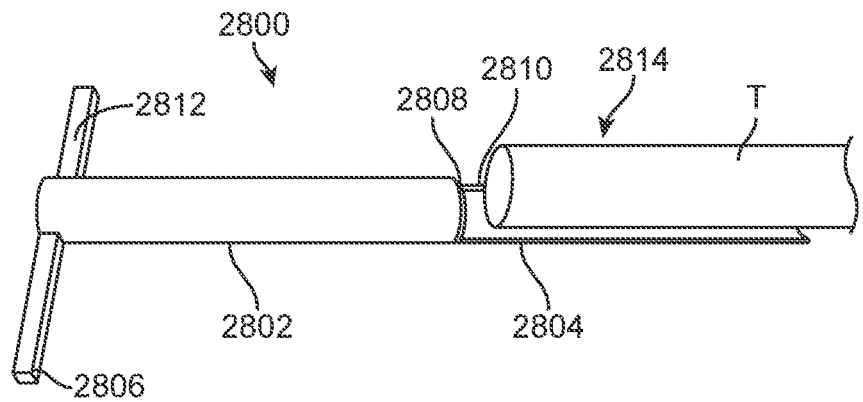
FIGS. 29A to 29C illustrate perspective views of a concentric clamp assembly having rotatable outer clamp and inner clamp members.
Figure 29B:
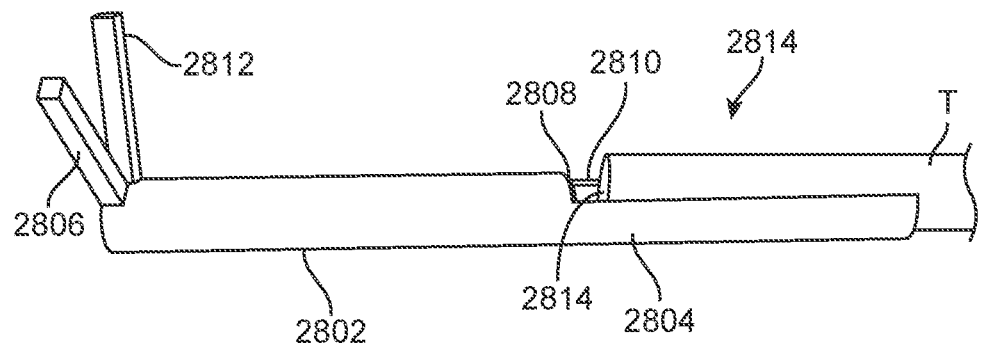
Figure 29C:
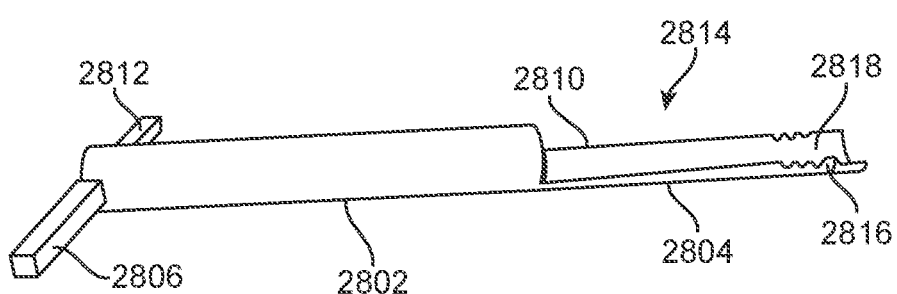

In yet another variation, FIGS. 29A to 29C show perspective views of a concentric clamp assembly 2800 having an outer clamp 2802 with a partially circumferential clamp portion 2804 and which is actuatable via a first handle 2806. The outer clamp 2802 may be coaxially aligned about an inner clamp and rotated relative to the inner clamp 2808 which also has a partially circumferential clamp portion 2810 and which is actuatable via a second handle 2812. Each of the clamp portions 2804, 2810 may define an open region 2814 within which a tissue region of interest T for treatment may be positioned. The inner and/or outer handles 2806, 2812 may be rotated relative to one another such that the clamp portions 2804, 2810 are drawn or clamped upon the tissue region T to maintain a position of the tissue as a separate coring needle is advanced over or within the clamp assembly 2800. The concentric clamp assembly 2800 may be utilized with any of the coring needle variations described herein.

Figure 30A:
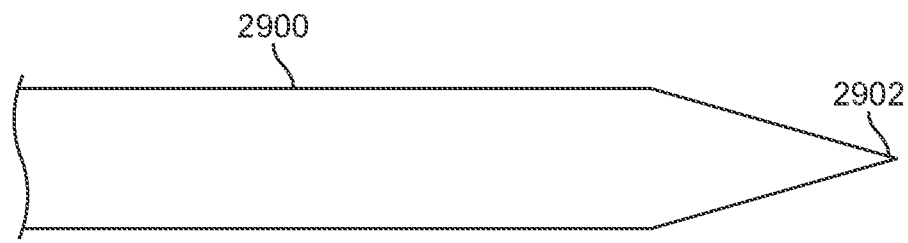
FIGS. 30A to 30E illustrate another variation of a clamp member which may be advanced within or externally of any of the clamping assemblies described herein.

FIGS. 30A to 30E show yet another variation of a clamp member which may be advanced within or externally of any of the clamping assemblies described herein, as practicable, by utilizing a clamp member having an integrated blade. FIG. 30A illustrates a top view of a clamp member 2900 having a piercing tip 2902.

Figure 30B:
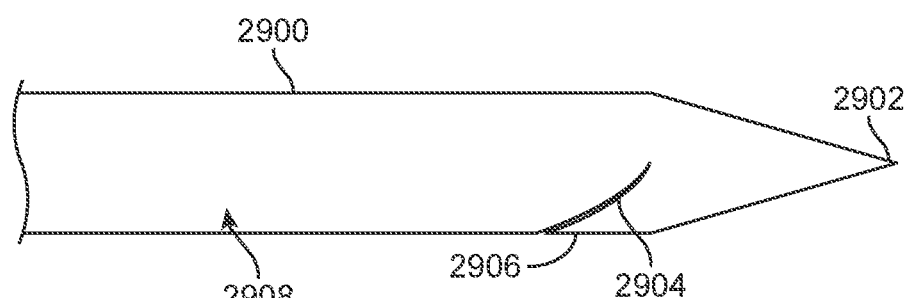
Figure 30C:
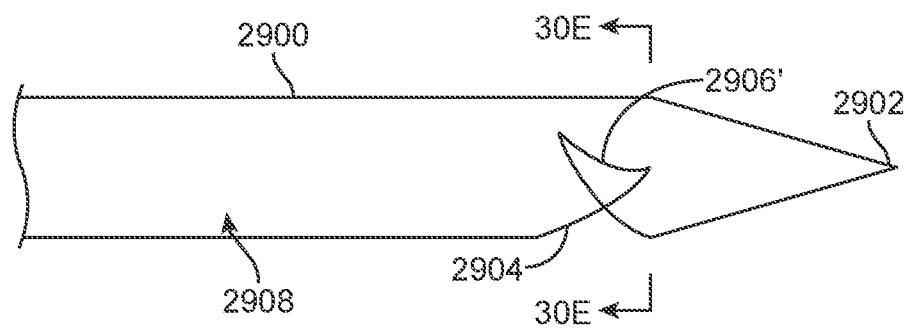
Figure 30D:
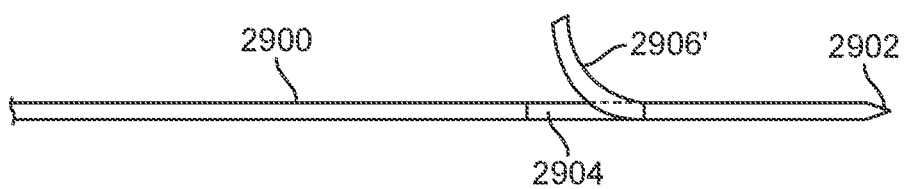

The clamp member 2900 may define a surface 2908 and may also have a reconfigurable blade 2906 along a side portion of the clamp member 2900. The blade 2906 may be defined by a slit or groove 2906 which extends at with a curvature or at an angle relative to the clamp member 2900, as shown in FIG. 30B. The clamp member 2900 may be advanced within the tissue, as described herein, and the blade 2906 may maintain its closed configuration to present a relatively smooth surface to the tissue. However, when the clamp member 2900 is retracted proximally within the tissue, the tip of the blade 2906 may gain purchase into the tissue and retract further such that the blade 2906 may extend with a curvature or at an angle relative to the surface 2908 and into its extended configuration 2906' into the tissue as the clamp member 2900 is further pulled proximally, as shown in the top view of FIG. 30C. FIG. 30D shows a side view illustrating how the blade in its extended configuration 2906' may project from the clamp member 2900 relative to the surface 2908.

Figure 30E:
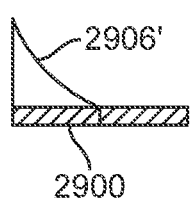

FIG. 30E shows an end view of the blade 2906' retracted relative to the surface 2908. With the blade in its retracted configuration, the clamp member 2900 may be used to increase an anchoring force within the tissue and/or the clamp member 2900 may be rotated to excise the cored tissue at the distal end of the enveloped tissue so as to facilitate truncation of the excised tissue prior to pulling it out of the turbinate tissue. Although a single clamp member 2900 is shown for illustrative purposes, two or more apposed clamp members may be utilized with any of the embodiments described herein. For example, two apposed clamp members 2900 may be positioned relative to one another so that each of the retracted blades 2906' may extend towards one another to facilitate cutting of the tissue.

FIGS. 31A to 31D show yet another variation of a coring needle which may also be used with any of the clamping assemblies described herein, as practicable, by utilizing a coring needle having an integrated blade shaped in a leaf-like configuration. FIGS. 31A and 31B show side and end views of a coring needle having a needle body 3000 which defines a lumen 3006 and a leaf-shaped blade 3004 defined by a slit or groove 3002. As the needle body 3000 is advanced distally over or along the clamp assembly, the body 3000 may present a relatively smooth surface to the tissue as the body 3000 is introduced and advanced within the tissue. Once the needle body 3000 has been advanced a suitable distance, it may be retracted proximally relative to the clamp and tissue such that a proximal edge of the blade 3004 may catch upon or make purchase with the tissue such that the blade is urged into its extended configuration 3004' and projects at least partially within the lumen, as shown in the perspective and end views of FIGS. 31C and 31D. The extended blade 3004' may be then rotated about its longitudinal axis to excise the cored tissue at the distal end of the cored tissue so as to facilitate truncation of the excised tissue prior to pulling it out of the turbinate tissue.

Yet another embodiment of the assembly is illustrated in FIGS. 32A and 32B which illustrates how a linear movement of a handle by the user can be translated to a rotational movement and advancement by a coring element. The handle 3108 may be attached to a linear translational element 3106 (such as a rack gear) which is engaged with a first rotational element 3102 (such as a pinion or bevel gear). As the handle 3108 is moved or pumped in a proximal linear direction, as indicated by arrow 3114, the first rotational element 3102 may be engaged by the teeth of linear translational element 3106 and urged to rotate in a first direction, as indicated by arrow 3116. The first rotational element 3102 may be engaged with a second rotational element 3100 (such as a bevel gear) which is positioned transverse relative to the first rotational element 3102 such that as the first rotation element 3102 is rotated in a first direction, the second rotational element 3100 may be forced to rotate as well as indicated by arrow 3118. The second rotational element 3100 may be coupled, e.g., to a rotational shaft 3110 which may in turn be engaged with an elongate element 3104 to which a coring needle 2210 may be attached. The elongate element 3104 may be threaded in a manner corresponding to the rotational shaft 3110. Alternatively, the second rotational element 3100 may be engaged directly with the elongate element 3104 which also may be threaded.

Rotation of the second rotational element 3100 may thus engage with the elongate element 3104 which may be guided or supported by support 3112 to advance the elongate element 3104 distally along the device, as indicated by arrow 3122. As the elongate element 3104 is advanced distally, it may also be rotated about its longitudinal axis, as indicated by arrow 3124, which may be coincident with the longitudinal axis of the device or with the coring needle 2210. In other alternatives, translational advancement of the elongate element 3104 and coring needle 2210 may be accomplished without rotation about its longitudinal axis. Rotation of the elongate element 3104 and coring needle 2210 may instead be omitted entirely or it may be selectively rotated independently of the translational advancement, if so desired.

Although described with a handle which may be translated proximally, the retraction of the handle may also be accomplished with a motor or actuator which may be in communication with a controller. The retraction may thus be performed automatically or when selected by the user to actuate the motor or actuator.

During use, and as described herein, the clamp members 2204A and 2204B may be advanced distally, e.g., into the turbinate tissue, with the coring needle 2210 set at a proximal position. As the handle 3108 is pulled or pumped proximally, the elongate element 3104 may be advanced distally while rotating about its longitudinal axis so that the coring needle 2210 is advanced and rotated over the clamp members 2204A, 2204B which are then urged towards one another, as indicated by respective arrows 3126A, 3126B, to clamp upon the turbinate tissue. As the coring needle 2210 is advanced and rotated, its cutting edge may cut the clamped turbinate tissue and envelope the tissue within the lumen of the coring needle 2210. Once the tissue has been sufficiently cored, the device may be pulled proximally to remove the cored turbinate tissue clamped and retained within the coring needle 2210.

The applications of the disclosed invention discussed above are not limited to the embodiments described, but may include any number of other applications and uses. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of resecting tissue, comprising:
advancing a clamping mechanism by inserting at least two distally extending members into the tissue region of interest and onto opposite sides of the tissue region of interest which is maintained in a stationary position relative to the clamping mechanism;
advancing an elongate coring needle having a distal end which defines a cutting mechanism along the clamping mechanism and into the tissue region of interest such that the coring needle is advanced over the distally extending members and urges the distally extending members towards one another; and
resecting the tissue region of interest by cutting the tissue region such that a defined volume of tissue is contained within a lumen of the coring needle.

2. The method of claim 1 wherein advancing a clamping mechanism comprises advancing the clamping mechanism within a nasal cavity and into proximity with turbinate tissue.

3. The method of claim 1 wherein advancing a clamping mechanism comprises clamping at least two distally extending members onto the opposite sides of the tissue region of interest.

4. The method of claim 1 further comprising advancing a spiraling needle into the defined volume of tissue to further resect the tissue region of interest.

5. The method of claim 4 wherein advancing a spiraling needle comprises distally translating one or more blades along the spiraling needle into the tissue region while rotating the needle.

6. The method of claim 4 wherein advancing a spiraling needle comprises controlling a depth of the needle within the tissue region via one or more stop elements or markers.

7. The method of claim 1 further comprising advancing a guiding needle into the tissue region of interest prior to advancing the clamping mechanism.

8. The method of claim 7 wherein at least two distally extending members of the clamping mechanism are advanced over the guiding needle and onto the tissue region of interest.

9. The method of claim 1 further comprising detaching the coring needle from a handle.

10. The method of claim 1 wherein advancing an elongate coring needle comprises rotating an outer coring member in a first direction while rotating an inner coring member in a second direction counter to the first direction.

11. The method of claim 1 further comprising controlling an operation of the device via a controller.

12. The method of claim 1 wherein advancing an elongate coring needle comprises controlling the coring element via a handle to manually control advancement of the coring needle into the tissue region of interest.

13. The method of claim 1 wherein advancing an elongate coring needle comprises controlling advancement of the coring needle via an electromechanical attachment.

14. The method of claim 1 wherein advancing an elongate coring needle further comprises rotating the coring needle about a longitudinal axis of the coring needle.

15. The method of claim 1 wherein prior to advancing an elongate coring needle, advancing a first plunger arm defining a tapered distal interface such that distal advancement of the first plunger arm relative to the clamping mechanism urges the distally extending members towards one another.

16. The device of claim 15 wherein advancing a first plunger arm further comprises advancing a second plunger arm positioned opposite to the first plunger arm such that distal advancement of the first plunger arm and the second plunger arm urges the distally extending members further towards one another.

17. The method of claim 1 wherein resecting the tissue region of interest comprises deploying a retractable blade along a side surface of the coring needle within the lumen.

18. The method of claim 1 further comprising visualizing the tissue region of interest.

19. A method of resecting tissue, comprising:
advancing a clamping mechanism within a nasal cavity and into proximity with turbinate tissue by inserting at least two distally extending members into the tissue region of interest and onto opposite sides of the tissue region of interest which is maintained in a stationary position relative to the clamping mechanism;
advancing an elongate coring needle having a distal end which defines a cutting mechanism along the clamping mechanism and into the tissue region of interest such that the coring needle is advanced over the distally extending members which are urged towards one another; and
resecting the tissue region of interest by cutting the tissue region such that a defined volume of tissue is contained within a lumen of the coring needle.

20. The method of claim 19 wherein advancing a clamping mechanism comprises clamping at least two distally extending members onto the opposite sides of the tissue region of interest.

21. The method of claim 20 further comprising visualizing the tissue region of interest.

22. The method of claim 19 further comprising advancing a spiraling needle into the defined volume of tissue to further resect the tissue region of interest.

23. The method of claim 22 wherein advancing a spiraling needle comprises distally translating one or more blades along the spiraling needle into the tissue region while rotating the needle.

24. The method of claim 22 wherein advancing a spiraling needle comprises controlling a depth of the needle within the tissue region via one or more stop elements or markers.

25. The method of claim 19 further comprising advancing a guiding needle into the tissue region of interest prior to advancing the clamping mechanism.

26. The method of claim 25 wherein at least two distally extending members of the clamping mechanism are advanced over the guiding needle and onto the tissue region of interest.

27. The method of claim 19 further comprising detaching the coring needle from a handle.

28. The method of claim 19 wherein advancing an elongate coring needle comprises rotating an outer coring member in a first direction while rotating an inner coring member in a second direction counter to the first direction.

29. The method of claim 19 further comprising controlling an operation of the device via a controller.

30. The method of claim 19 wherein advancing an elongate coring needle comprises controlling the coring element via a handle to manually control advancement of the coring needle into the tissue region of interest.

31. The method of claim 19 wherein advancing an elongate coring needle comprises controlling advancement of the coring needle via an electromechanical attachment.

32. The method of claim 19 wherein advancing an elongate coring needle further comprises rotating the coring needle about a longitudinal axis of the coring needle.

33. The method of claim 19 wherein prior to advancing an elongate coring needle, advancing a first plunger arm defining a tapered distal interface such that distal advancement of the first plunger arm relative to the clamping mechanism urges the distally extending members towards one another.

34. The device of claim 33 wherein advancing a first plunger arm further comprises advancing a second plunger arm positioned opposite to the first plunger arm such that distal advancement of the first plunger arm and the second plunger arm urges the distally extending members further towards one another.

35. The method of claim 19 wherein resecting the tissue region of interest comprises deploying a retractable blade along a side surface of the coring needle within the lumen.

* * * * *